US009791353B2

(12) United States Patent
Saaski et al.

(10) Patent No.: US 9,791,353 B2
(45) Date of Patent: Oct. 17, 2017

(54) CONCENTRATOR

(75) Inventors: Elric W. Saaski, Bothell, WA (US); Charles C. Jung, Snohomish, WA (US)

(73) Assignee: RESEARCH INTERNATIONAL, INC., Monroe, WA (US)

( * ) Notice: Subject to any disclaimer, the term of this patent is extended or adjusted under 35 U.S.C. 154(b) by 2111 days.

(21) Appl. No.: 12/231,207

(22) Filed: Aug. 29, 2008

(65) Prior Publication Data

US 2010/0050750 A1 Mar. 4, 2010

(51) Int. Cl.
*G01N 1/22* (2006.01)
*G01N 1/40* (2006.01)
*G01N 15/06* (2006.01)

(52) U.S. Cl.
CPC ......... *G01N 1/2205* (2013.01); *G01N 1/4077* (2013.01); *G01N 15/0618* (2013.01); *G01N 2001/4088* (2013.01)

(58) Field of Classification Search
CPC ............... G01N 1/2205; G01N 1/4077; G01N 15/0618; G01N 2001/4088
USPC .......................................... 73/863.41, 863.45
See application file for complete search history.

(56) References Cited

U.S. PATENT DOCUMENTS 4,301,002 A 11/1981 Loo
4,580,440 A 4/1986 Reid et al.
4,670,135 A 6/1987 Marple et al.
4,689,052 A 8/1987 Ogren et al.
4,718,268 A 1/1988 Reid et al.
4,767,524 A 8/1988 Yeh et al.
4,972,957 A 11/1990 Liu et al.
5,183,481 A 2/1993 Felder
5,347,845 A 9/1994 Kepler
5,533,406 A 7/1996 Geise
5,788,741 A * 8/1998 Burton et al. .................... 95/32
5,855,652 A 1/1999 Talley
5,858,043 A 1/1999 Geise
5,932,795 A 8/1999 Koutrakis et al.
5,967,332 A 10/1999 Willeke
6,010,554 A 1/2000 Birmingham et al.
(Continued)

FOREIGN PATENT DOCUMENTS

SU 1142663 A * 2/1985
SU 1751603 A1 * 7/1992

OTHER PUBLICATIONS

Chinese Office Action of Mar. 31, 2011 regarding the corresponding Chinese Patent Application No. 200910166843.8, 4 pages; and an English translation thereof, 5 pages.

*Primary Examiner* — Helen Kwok
*Assistant Examiner* — Nashmiya Fayyaz
(74) *Attorney, Agent, or Firm* — Gregory W. Moravan

(57) ABSTRACT

A concentrator that is operable to concentrate particles of target material from a high flow rate sampled airflow into a low flow rate secondary airflow. The concentrator may have an array of radially arranged blades. Each blade may have a sampled airflow inlet that uses centrifugal force to concentrate the particles into a central portion of the sampled airflow passing through it. Downstream, the blade may also have primary airflow outlets and knife-edged secondary airflow inlets that divide the sampled airflow into a pair of lateral, high flow rate primary airflows from which the particles have been depleted, and a central, low flow rate secondary airflow which carries the concentrated particles.

37 Claims, 19 Drawing Sheets

(56) References Cited

U.S. PATENT DOCUMENTS

| | | | |
|---|---|---|---|
| 6,062,392 | A | 5/2000 | Birmingham et al. |
| 6,101,886 | A | 8/2000 | Brenizer et al. |
| 6,120,573 | A | 9/2000 | Call et al. |
| 6,156,212 | A | 12/2000 | Rader et al. |
| 6,170,342 | B1 | 1/2001 | John |
| 6,284,025 | B1 | 9/2001 | Kreisberg et al. |
| 6,290,065 | B1 | 9/2001 | Kenning et al. |
| 6,402,817 | B1 | 6/2002 | Bergman |
| 6,435,043 | B1 | 8/2002 | Ferguson et al. |
| 6,446,514 | B1 | 9/2002 | Danylewych-May et al. |
| 6,478,856 | B1 * | 11/2002 | Leibholz et al. ............... 95/268 |
| 6,688,187 | B1 | 2/2004 | Masquelier |
| 6,695,146 | B2 | 2/2004 | Call et al. |
| 6,698,592 | B2 | 3/2004 | Kenning et al. |
| 6,746,503 | B1 | 6/2004 | Benett et al. |
| 6,792,795 | B2 | 9/2004 | Jones et al. |
| 6,823,714 | B2 | 11/2004 | Megerle |
| 6,827,761 | B2 | 12/2004 | Graham |
| RE38,797 | E | 9/2005 | Linker et al. |
| 6,978,657 | B1 | 12/2005 | Baumann et al. |
| 6,990,846 | B2 | 1/2006 | Sioutas |
| 7,019,640 | B2 | 3/2006 | Canich et al. |
| 7,032,467 | B2 | 4/2006 | Yoon |
| 7,100,424 | B2 | 9/2006 | Wilson |
| 7,113,277 | B2 | 9/2006 | Craig |
| 7,125,437 | B2 | 10/2006 | Bryden et al. |
| 7,151,447 | B1 | 12/2006 | Willms et al. |
| 7,158,028 | B1 | 1/2007 | Ghahramani |
| 7,173,257 | B1 | 2/2007 | Warrick et al. |
| 7,178,380 | B2 | 2/2007 | Shekarriz et al. |
| 7,188,513 | B2 | 3/2007 | Wilson |
| 7,201,879 | B2 | 4/2007 | Hill et al. |
| 7,216,548 | B2 | 5/2007 | Kurita et al. |
| 7,232,477 | B2 | 6/2007 | Rodgers |
| 7,261,007 | B2 | 8/2007 | Haglund et al. |
| 7,265,669 | B2 | 9/2007 | Call et al. |
| 7,275,453 | B2 | 10/2007 | Ishikawa et al. |
| 7,316,152 | B2 | 1/2008 | Strohmeyer et al. |
| 7,324,921 | B2 | 1/2008 | Sugahara et al. |
| 7,325,465 | B2 | 2/2008 | Solomon et al. |
| 7,390,339 | B1 | 6/2008 | Warrick et al. |
| 7,394,363 | B1 | 7/2008 | Ghahramani |
| 7,468,672 | B2 | 12/2008 | Harden et al. |
| 7,501,624 | B1 | 3/2009 | Farrell et al. |
| 7,503,204 | B2 | 3/2009 | Strohmeyer et al. |
| 7,846,228 | B1 | 12/2010 | Saaski et al. |
| 2004/0020267 | A1 | 2/2004 | Megerle |
| 2004/0045342 | A1 | 3/2004 | Jones et al. |
| 2004/0226342 | A1 | 11/2004 | Taricco |
| 2004/0233055 | A1 | 11/2004 | Canich et al. |
| 2005/0081653 | A1 | 4/2005 | Arabian et al. |
| 2006/0027751 | A1 | 2/2006 | Kurita et al. |
| 2006/0042397 | A1 | 3/2006 | Kurita et al. |
| 2006/0169025 | A1 | 8/2006 | Wilson |
| 2006/0226998 | A1 | 10/2006 | Wilson |
| 2006/0257287 | A1 | 11/2006 | Call et al. |
| 2007/0266771 | A1 | 11/2007 | Goldson et al. |
| 2007/0277589 | A1 | 12/2007 | Harden et al. |
| 2008/0055075 | A1 | 3/2008 | Fano |
| 2008/0129493 | A1 | 6/2008 | Fuentes et al. |
| 2008/0251514 | A1 | 10/2008 | Fitzpatrick et al. |
| 2009/0184818 | A1 | 7/2009 | Murphy et al. |
| 2010/0186483 | A1 | 7/2010 | Saaski |

* cited by examiner

Fig. 8
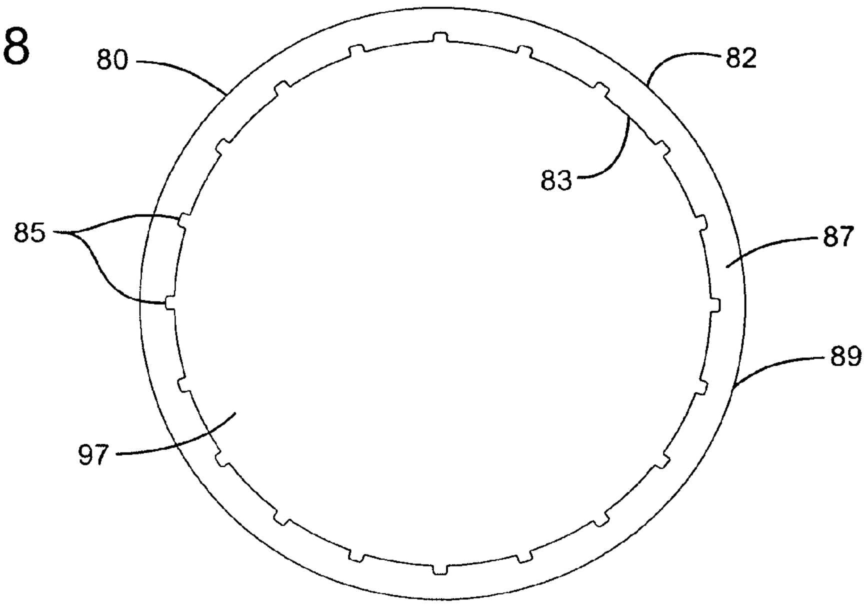
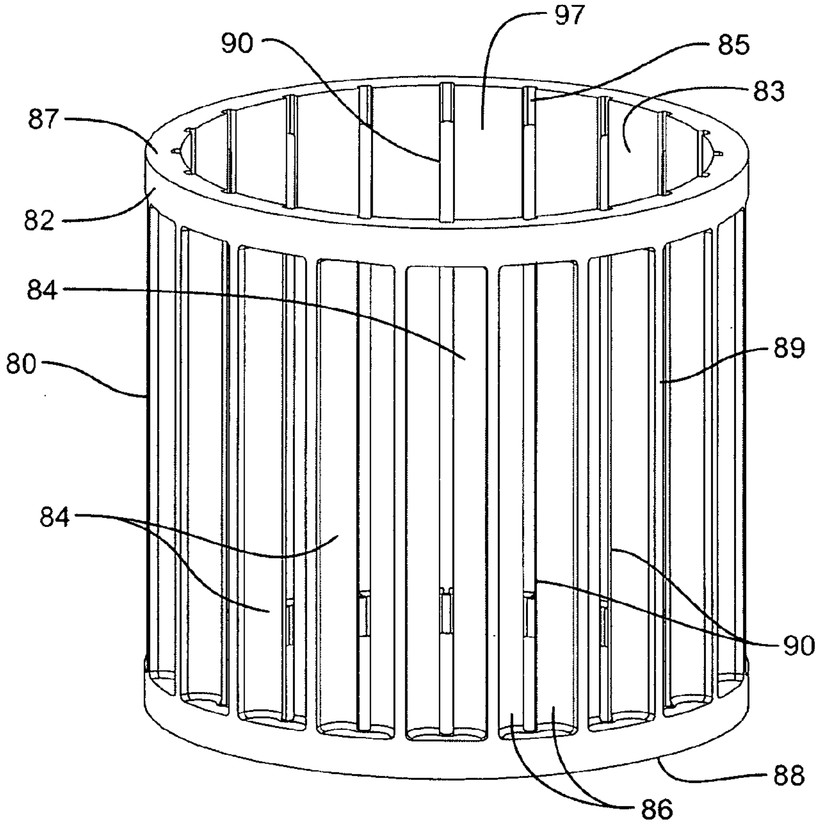
Fig. 8A

Fig. 9
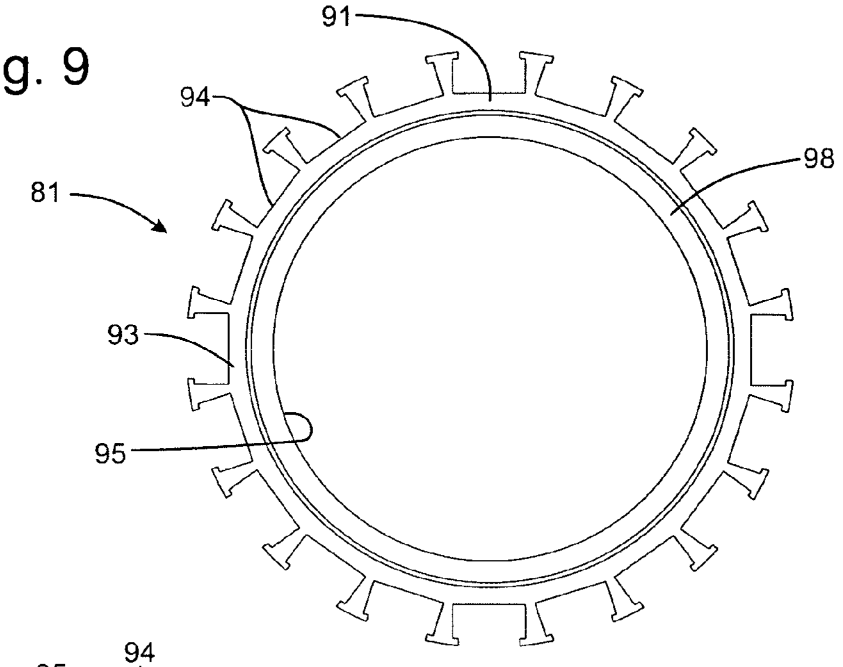
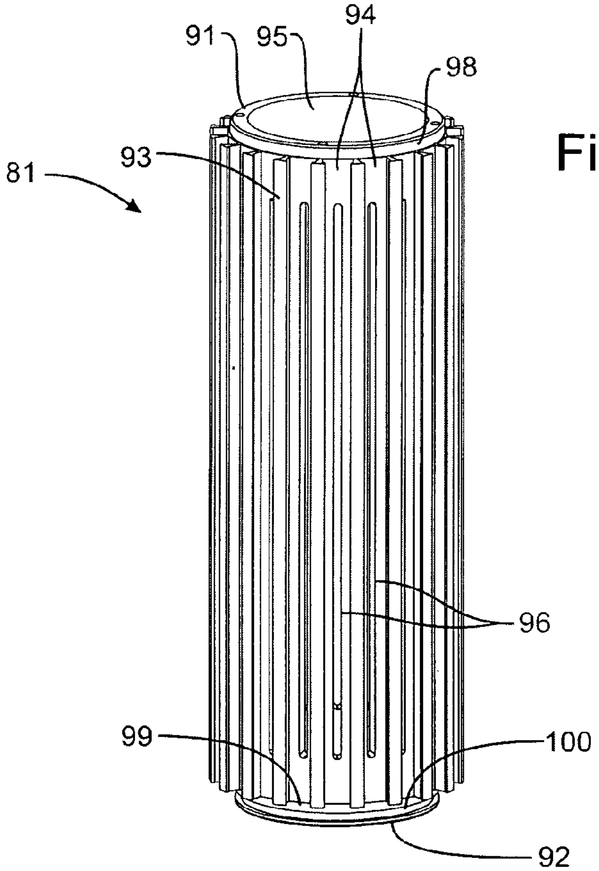
Fig. 9A

CONCENTRATOR

STATEMENT REGARDING FEDERALLY SPONSORED RESEARCH OR DEVELOPMENT

The invention was not made by an agency of the United States Government or under a contract with an agency of the United States Government.

BRIEF DESCRIPTION OF THE SEVERAL VIEWS OF THE DRAWING

FIG. 8 is a top plan view of the air processor 12's outer hub 80;

FIG. 8A is a perspective view of the air processor 12's outer hub 80, taken from an upper aspect;

FIG. 9 is a top plan view of the air processor 12's inner hub 81;

FIG. 9A is a perspective view of the air processor 12's inner hub 81, taken from an upper aspect;

DETAILED DESCRIPTION OF THE INVENTION

Background

Figure 1:
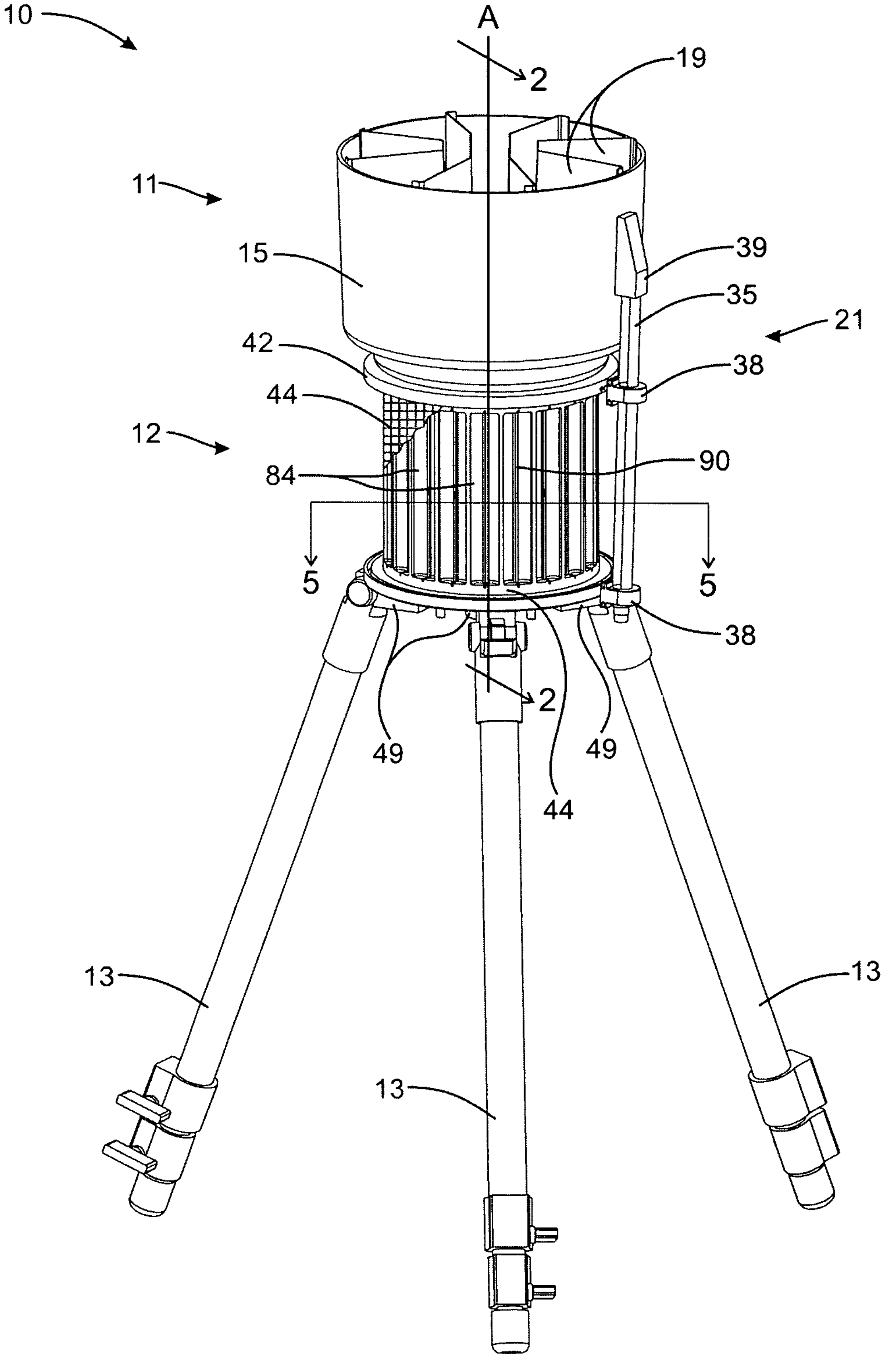
FIG. 1 is an assembled perspective view of the concentrator 10, taken from an upper aspect, shown mounted on tripod legs 13.

Many human activities are influenced by the presence of a variety of airborne particles. For example, a great number of natural pests and pathogens comprise airborne microscopic biological particles such as molds, fungi, bacteria, viruses, and multi-celled microorganisms. The collection and removal of such particles from the air, such as for observation, identification, examination, testing or analysis, is often made difficult by their small size, fragility, low density, and low volumetric concentration in the air. Unfortunately, it may take only one such particle to create infection or illness, or to contaminate a hospital area.

In addition, clean rooms require extremely low concentrations of both organic and inorganic airborne particles to minimize wafer defects and to maintain high device yields. Further, counter-terrorism efforts often hinge on the collection and removal from the air of small numbers of airborne particles such as pathogenic bacteria, their spores, or weaponized viruses or toxins, so that the particles are available for observation, identification, examination, testing or analysis. In addition, the monitoring of luggage for explosives is often now based on the collection and removal from the air of microscopic particles of explosives that may be as small as 1 micron in diameter.

The airborne particles of interest may be called particles containing target material, which may be particles containing any material of interest, such as any liquid, solid, organic, inorganic, biological or non-biological material, or mixtures thereof. In the description which follows, the movement of particles containing target material will be described strictly by way of non-limiting example, it being understood that the same or similar description may apply equally well to the movement of any other kind of particle.

The term "air" is used broadly, so that it may be any gas or mixture of gasses other than air.

Several difficulties are often encountered in removing airborne particles containing target material from large volumes of sampled air. First, a sampled air collection device that produces a sampled airflow 102 having a high flow rate may be heavy and bulky. Second, a high flow rate sampled air collection device may be difficult to use with many types of conventional air samplers, particle analyzers, and analytical devices which are designed to be used with a sampled airflow 102 having a low flow rate, such as a flow rate of 500 liters per minute (LPM), or less.

An air sampler may be any device that removes particles containing target material from an airflow, such as from the sampled airflow 102, so that the particles containing target material may be observed, identified, examined, tested or analyzed. A particle analyzer may be any device that determines the size, concentration, nature, and/or approximate composition (such as biological versus non-biological) of the particles of target material. An analytical device may be any device that detects and/or identifies targeted constituent materials in the particles, including explosives, drugs, bacteria, spores, viruses, toxins, animal and plant pathogens, and industrial chemicals, as nonlimiting examples.

Third, a sampled airflow 102 having a high flow rate often results in high air velocities of the sampled air that can be injurious to certain kinds of particles containing target material that are delicate, such as organisms, due to the physical shear forces or desiccation caused by the high air velocities.

Fourth, commercially available concentrators (devices for concentrating particles containing target materials from a sampled airflow 102), typically require high overall pressure differences for correct operation. Air handlers such as fans, blowers and air turbines that can support those types of pressure differences are often heavy, large in size, and inefficient, consuming large amounts of power for a comparatively small sampled airflow 102. This may not be an issue if the sampled airflow 102 is small, since the total electrical power consumption of the concentrator and its air handler may still be acceptable. However, for applications where the sampled airflow 102 is greater than about 1000 liters/minute, the efficiency of both the concentrator and air handler become very important. For this reason, commercially available concentrator systems are typically not appropriate or available for portable applications where it is desirable to process large quantities of sample air, such as the sampling of shipping containers and ship's holds, train cars, agricultural settings, open air markets, food processing facilities and large public venues such as auditoriums and arenas, office buildings, and shopping centers.

The Concentrator 10

Accordingly, in order to address one or more of the difficulties mentioned above, the concentrator 10 may be a relatively small, lightweight, low power consuming, and portable device that can produce and process a sampled airflow 102 having a high flow rate, and concentrate the particles containing target material therein into a secondary airflow 104 having a much lower flow rate that may match the input requirements of any conventional air sampler, particle analyzer, or analytical device.

In view of all of the disclosures herein, it is understood that the concentrator 10 may be designed to produce a secondary airflow 104 having any desired flow rate that matches the input requirements of any particular air sampler, particle analyzer, or analytical device, regardless of whether or not the particular air sampler, particle analyzer, or analytical device is a commercial, off-the-shelf device.

By way of example, the example concentrator 10 that is described below may be small, lightweight, low power consuming, and portable. It may produce and process a sampled airflow 102 having a relatively high flow rate of about 3,000 to 3,600 LPM, dividing airflow 102 into a primary airflow 103 and a secondary airflow 104. The sum of the flow rates of the primary and secondary airflows 103, 104 will be equal to the flow rate of the sampled airflow 102.

The example concentrator 10 may concentrate into the secondary airflow 104 on the order of about 60% to about 80% of the particles of target material that were present in the sampled airflow 102. The secondary airflow 104 may have a flow rate that is nominally 1% to 10% of the flow rate of the primary airflow 103. The secondary airflow 104, and the concentrated particles containing target material that it carries, may then be conveyed in any suitable way to any suitable air sampler, particle analyzer, or analytical device. This entire process may be accomplished using only 50 to 100 watts of electric power.

Figure 2:
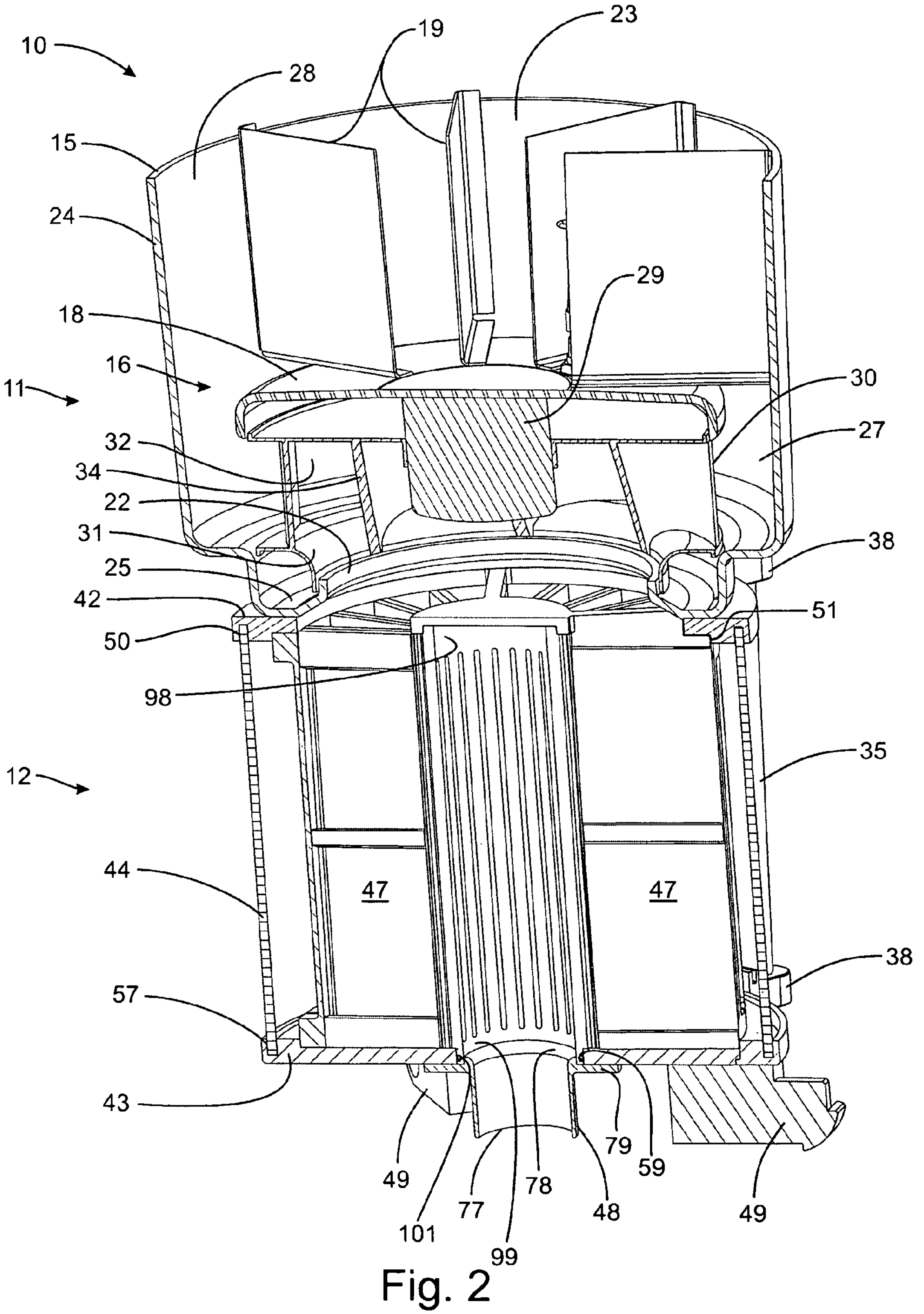
FIG. 2 is cross-sectional, perspective view of the concentrator 10, taken along line 2-2 of FIG. 1, and taken from an upper aspect.

As best seen in FIGS. 1-2, concentrator 10 may comprise two main components, i.e., a fan assembly 11 and an air processor 12. Regarding the orientation of the concentrator 10, by way of example it is illustrated as having its central longitudinal axis A oriented vertically, so that its fan assembly 11 is located directly above its air processor 12. Accordingly, by way of example and for simplicity and ease of understanding, the various parts of the concentrator 10 and their relationships with respect to each other will be described herein with respect to the vertically oriented concentrator 10 that is illustrated.

However, it is understood that the concentrator 10's axis A may be tipped at any angle up to 180 degrees from the vertical. For example, if its axis A were tipped 90 degrees from the vertical, then its fan assembly 11 and its air processor 12 would be located side by side; and if its axis A were tipped 180 degrees from the vertical, then its air processor 12 would be located directly above its fan assembly 11.

The concentrator 10 may be mounted in any suitable way, at any desired height above the surface which supports it, with any desired orientation of its axis A, such as by the use of length-adjustable tripod legs 13, or by being mounted in any suitable way to one or more pieces of other equipment.

As an alternative, the fan assembly 11 and the air processor 12 may not be connected directly together, but may be remotely connected together in any suitable way by any suitable device such as by any suitable air conduit that extends between the air outlets 55 in the assembly 12's top plate 42 and the air inlet 22 of the fan plenum 15 or the air inlet 31 of the fan 16.

The concentrator 10, its fan assembly 11, and its air processor 12 may all be called "negative pressure" devices because its fan assembly 11 is operable to create a negative air pressure in the primary airflow outlets 55 in the air processor 12's top plate 42, so that the flow of the sampled air through the assembly 12 is at least partially driven by the ambient, higher pressure sample air that surrounds the air processor 12.

As an alternative, any other suitable fan assembly 11 of any suitable construction that is operable to apply a negative air pressure to the air outlets 55 in the air processor 12's top plate 42 may be used in lieu of the fan assembly 11 that is illustrated and described herein.

As a further alternative, the fan assembly 11 may be eliminated, so that the concentrator 10 may comprise just a negative pressure air processor 12. Such a concentrator 10 may then be used by connecting it in any suitable way to any suitable source of negative air pressure.

As seen in FIG. 1, the concentrator 10 may be utilized by being located directly within the air to be sampled, such as if it were placed in a room full of the air to be sampled. Alternatively, the concentrator 10 may be utilized by being located remotely from the air that is to be sampled, such as is illustrated in FIG. 23, in which case the sampled airflow 102 is delivered to the concentrator 10 in any suitable way, such as through an input duct 141.

In view of the disclosures herein, it will be appreciated that the concentrator 10 may be designed to produce and process a sampled airflow 102 having any desired flow rate. This may be done in any suitable way, such as by scaling the concentrator 10 up or down with respect to its size and its number of parts, by increasing the negative air pressure that is applied to its air processor 12, or by modifying the concentrator 10 in any other suitable way.

Concentrator 10B

Figure 22:
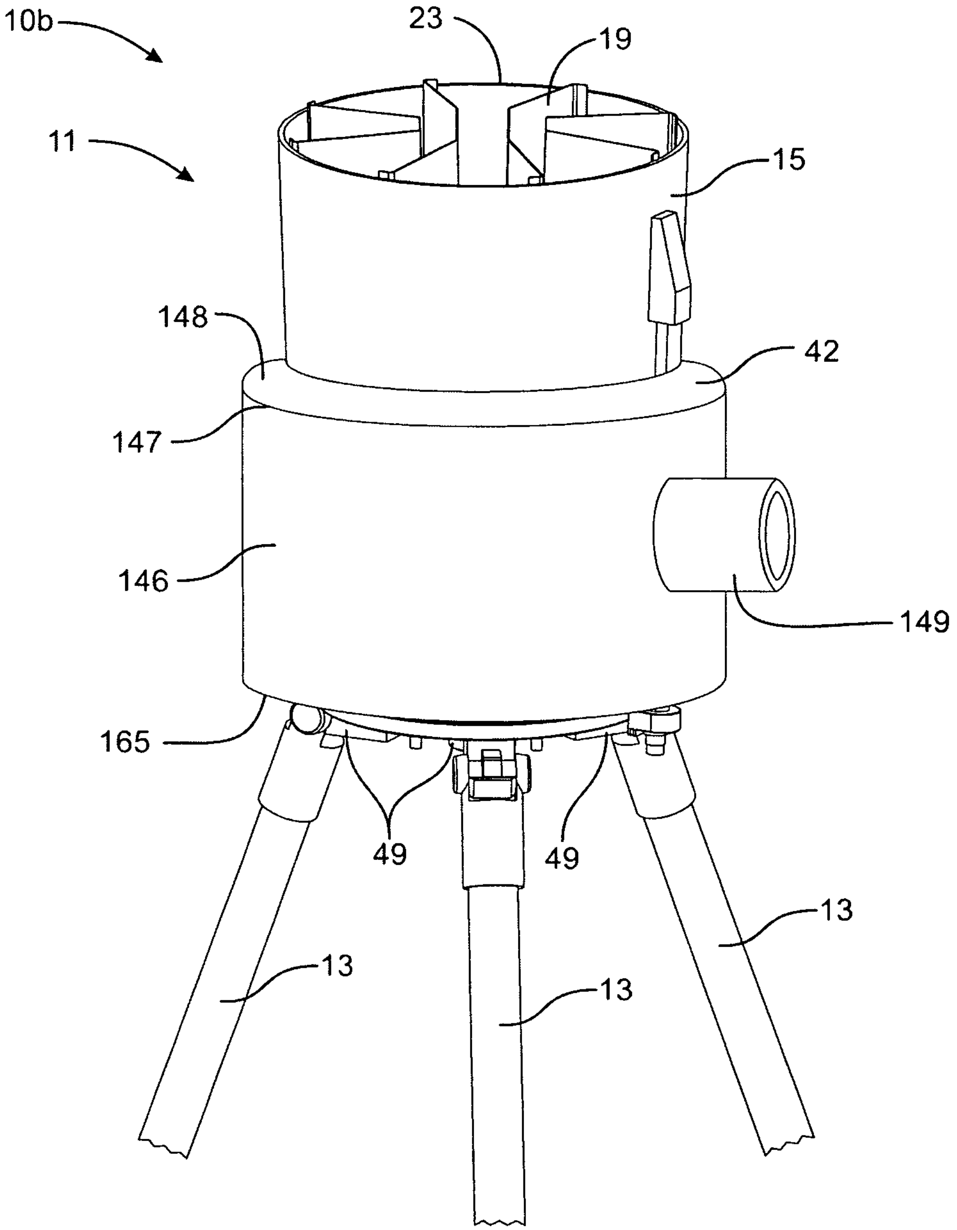
FIG. 22 is a perspective view of a concentrator 10*b*, taken from an upper aspect.
Figure 23:
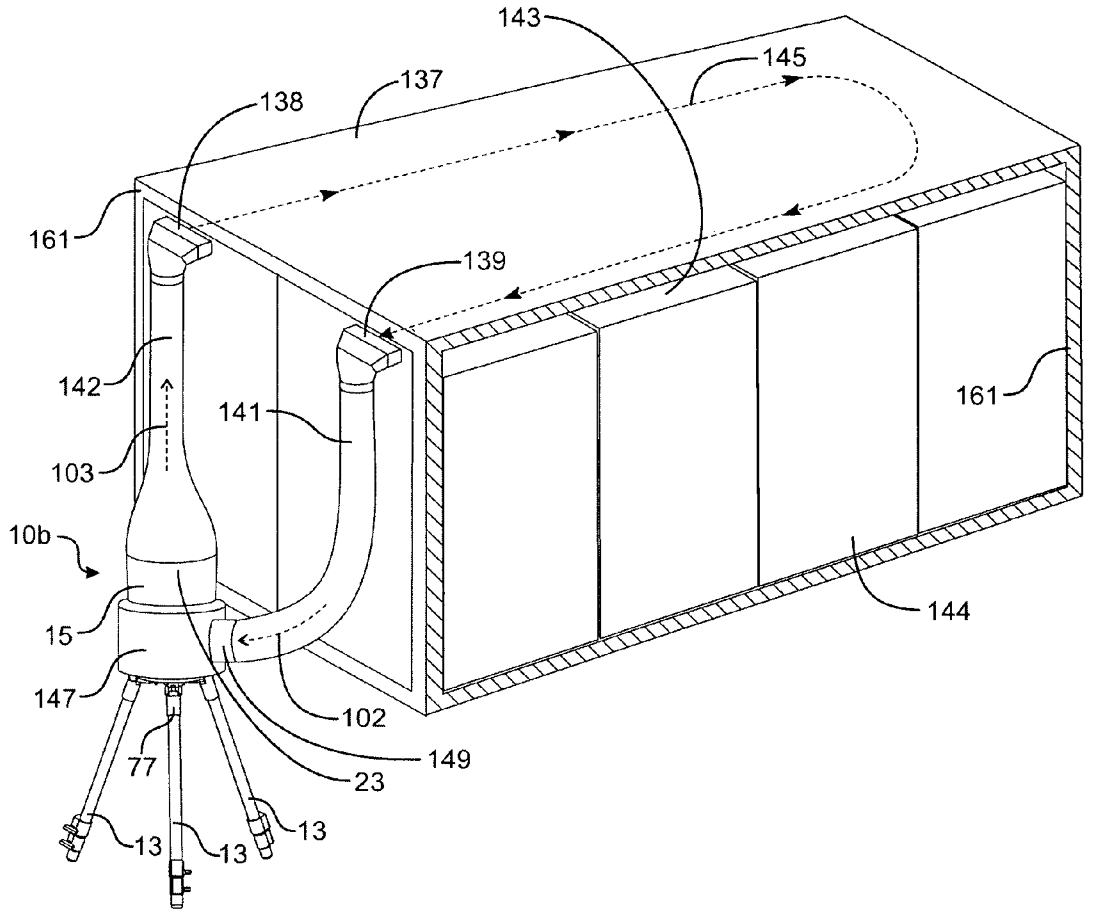
FIG. 23 is a perspective view, partly in cross section of a concentrator 10*b* being used to interrogate a shipping container 137.

Turning now to FIGS. 22 and 23, an alternative, "shrouded" concentrator 10*b* is illustrated. The concentrator 10*b* of FIG. 22 may be the same as, or at least similar to, the concentrator 10 of FIGS. 1-16 and the concentrator 10*a* of FIGS. 17-19 in all respects, except for those differences which will be made apparent by all of the disclosures herein The concentrator 10*b* may further comprise a hollow annular shroud 147 having an inlet 149 of any suitable size, shape, and construction. There may be more than one inlet 149. The shroud 147 may enclose the outer surface of the outer hub 80, and be sized to provide an annular air chamber around the outer surface of the outer hub 80. The shroud 147 may be of any suitable size, shape and construction, and may be assembled to the air processor 12 in any suitable way, such as by being assembled to the top and bottom plates 42, 43 of the air processor 12.

The fan assembly 11 may be operable to apply a negative air pressure to the air chamber within the shroud 147, and may at the same time be operable to apply a positive air pressure within the fan plenum 15. The negative air pressure may cause the sampled airflow 102 to flow into the shroud 147 through its inlet 149, and to then pass through the concentrator 10*b*'s air processor 12. The positive air pressure may then cause the primary airflow 103 to flow out of the concentrator 10*b* through its fan plenum 15.

The concentrator 10*b* may further comprise any suitable optional input and output ducts 141, 142 of any suitable size, shape and construction which may be connected in any suitable way to the concentrator 10*b*'s inlet 149 and fan plenum 15, respectively.

The concentrator 10*b* may be used in any suitable way. For example, as seen in FIG. 23 an input duct 141 may be connected between a shipping container 137's outlet port 139 and the concentrator 10*b*'s inlet 149; while an output duct 142 may be connected between the concentrator 10*b*'s fan plenum 15 and the shipping container 137's inlet port 138.

The negative air pressure created by the concentrator 10*b* may then cause a sampled airflow 102 to flow from the sample air within the airspace 143 within the shipping container 137, through the input duct 141, into the shroud 147's inlet 149, and through the concentrator 10*b*'s air processor 12. The positive air pressure created by the concentrator 10*b* within its fan plenum 15 may then cause the primary airflow 103 to flow from the fan plenum 15, through the output duct 142 and back into the shipping container 137 through its inlet port 138.

Thus, it has been discovered that the concentrator 10*b* may be operable to create a closed circuit airflow so that the flow of the sampled airflow 102 through the air processor 12 is driven by a combination of positive and negative air pressure created by concentrator 10*b*'s fan assembly 11.

As alternatives, the output duct 142 may be eliminated, so that the primary airflow 103 from the fan plenum 15 may be discharged into the air surrounding the concentrator 10*b*. As a further alternative, the shroud 147's inlet 149 may be located on any suitable surface of the shroud 147 other than on its cylindrical surface 146 as is illustrated in FIGS. 22-23. For example, one or more inlets 149 of any suitable size shape and construction may be located on the top or bottom end surfaces 148, 165 of the shroud 147.

Concentrator 10*b* may be particularly desirable for vehicle- or aircraft-mounted applications. For example, if its inlet 149 is located in either the top or bottom end surfaces 148, 165 of its shroud 147 (see FIG. 22), and if such an inlet 149 is oriented in the direction of travel, then the kinetic pressure created by vehicle or aircraft forward motion can be used to at least assist in driving a sampled airflow 102 through its air processor 12. By sizing the diameter of shroud 147 so there is no substantive internal pressure difference between its top and bottom end surfaces 148, 165 during operation, then the entire outer surface 82 of its outer hub 80 will be uniformly pressurized by the sampled airflow 102, assuring uniform inward radial flow of the sampled airflow 102 at each sampled airflow inlet pocket 84 in the outer surface of its outer hub 80, independent of vehicle or aircraft forward velocity. The kinetic pressure in some cases may be adequate to totally drive the sampled airflow 102, eliminating the need for fan assembly 11. In such a case the primary airflow 103 may exit the air processor 12 through any suitable respective primary airflow outlet 55 in the air processor 12's end plate 42, 43 that is located at the opposite end of shroud 147 from where inlet 149 is located. The primary airflow 103 may exit through either end plate 42, 43.

As alternatives, the concentrators 10, 10*a* may also comprise a shroud 147, inlet 149, and optional input and output ducts 141, 142; and may be used in ways that are the same as, or at least similar to the ways in which the concentrator 10*b* may be used.

Fan Assembly 11

Figure 3:
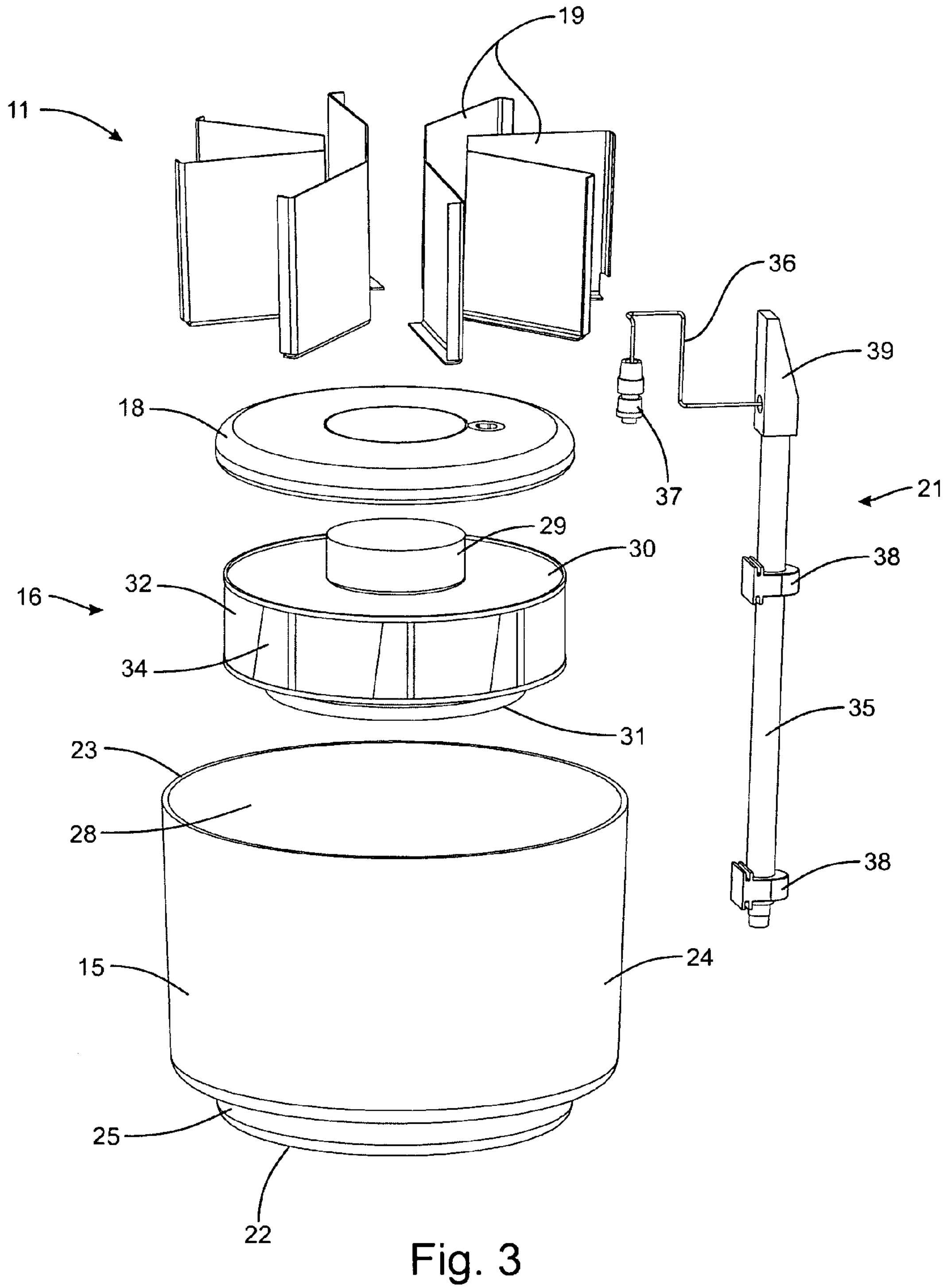
FIG. 3 is an exploded perspective view of the concentrator 10's fan assembly 11, taken from an upper aspect.

Returning now to the concentrator 10 of FIGS. 1-16, as best seen in FIGS. 2-3, the fan assembly 11 may comprise a fan plenum 15; a fan 16 having a fan motor 29; a fan plate 18; and airflow-straightening vanes 19. A power cable assembly 21 for providing power to the fan motor 29 may, or may not, be part of the fan assembly 11.

As best seen in FIGS. 1 and 3, the power cable assembly 21 may comprise a conduit 35, a pair of through mounting clips 38 for mounting the conduit 35 to the air processor 12, a right angle mounting clip 39 for mounting the conduit 35 to the plenum 15, a through connector 37 that may be assembled to the fan plate 18, and an electrical wire 36 for supplying power to the fan motor 29. The electrical wire 36 may be routed sequentially through the conduit 35, through the right angle mounting clip 39 into the plenum's air chamber 28, and through the connector 37 in the fan plate 18 to the fan motor 29.

The fan 16 may also have an impeller 30, an air inlet 31 in the impeller 30, impeller vanes 34, and air outlets 32 between the impeller vanes 34. Although a high speed electric centrifugal fan 16 is illustrated in the Figures, any suitable fan 16, having any suitable size, shape, power, construction and air moving capacity may be used, whether electric or not, depending on such factors as, for example, the desired flow rate of the sampled airflow 102 through the concentrator 10 and the space available in or on fan assembly 11 for mounting the fan 16. A large variety of air movers are available that may be suitable for use as fan 16. These air movers, such as fans and blowers, are frequently optimized for a specific quality, such as high flow volume, low or high-pressure delivery, and/or positive or negative pressure operation. Centrifugal fans with backward-curved blade designs provide a particularly satisfactory combination of electric-to-pneumatic efficiency and operating flexibility and are a preferred air mover for integration with concentrator 10.

The fan motor 29 and impeller 30 are shown diagrammatically in the Figures, it being understood that any suitable part of the fan motor 29 may be assembled to the fan plate 18 in any suitable way, so that the impeller 30 may rotate with respect to the part of the fan motor 29 that is assembled to the fan plate 18.

The fan plenum 15 may have an air inlet 22; an air outlet 23; a sidewall 24; a mounting flange 25; a spacing flange 26;

an annular air discharge chamber 27 between the impeller 30 and the plenum 15's sidewall 24; and a cylindrical discharge air cavity between the fan plate 18 the plenum 15's outlet 23. Although the plenum 15 is illustrated as being symmetrical about the axis A, it may not be symmetrical about the axis A. Although the plenum 15's sidewall 24 is illustrated as having a circular cross-sectional profile of constant size and shape along its length, it may have any other suitable geometric or non-geometric cross-sectional profile, and its cross-sectional area and shape may not be constant along its length.

Although eight airflow-straightening vanes 19 are illustrated, there may be fewer, more, or no vanes 19. If the concentrator 10 comprises one or more vanes 19, each vane 19 may have any suitable size, shape and construction other than that illustrated, and all of the vanes 19 may or may not have the same size, shape and construction.

To assemble the fan assembly 11, the fan plate 18 may be assembled to fan motor 29; and the lower ends of the vanes 19 may be assembled to the top of the fan plate 18. To assemble the fan 16 within the plenum 15, the fan 16 (and its assembled fan plate 18 and vanes 19), may be inserted through the plenum 15's air outlet 23, and then the outer edges of the vanes 19 may be assembled to the plenum 15's sidewall 24. When the fan 16 has been assembled within the plenum 15 there may be a small clearance between the air inlet 31 of its impeller 30 and the air inlet 22 and mounting flange 25 of the fan plenum 15.

Although the air inlets 22, 31 are illustrated as being concentrically arranged, with the inlet 31 being sized larger than the inlet 22, the inlets 22, 31 may have any suitable sizes and any suitable arrangement with respect to each other. For example, they may be concentrically arranged with the inlet 22 being sized larger than the inlet 31, or the inlets 22, 31 may have the same size and be arranged end to end.

The various parts of the fan assembly 11 may be assembled together in any suitable way such as by using fasteners; interference fits; friction fits; barbed, threaded, bonded, glued or welded connections; splines; keys; or mechanical couplers.

During operation of the concentrator 10 the primary airflow 103 from its air processor 12 may be urged by the fan 16 to flow into the air inlet 22 of the plenum 15 from the primary airflow outlets 55 in the air processor 12. The primary airflow 103 may then be urged by the fan 16 to flow through the air inlet 31 of the fan 16's impeller 30, and out through the air outlets 32 of the impeller 30. The sidewall 24 of the plenum 15 may then route the air discharged by the fan 16 upwardly through the plenum 15's air chambers 27, 28, between the airflow straightening vanes 19, and out through the plenum 15's air outlet 23. Due to the plenum 15 and the vanes 19, the primary airflow 103 may be discharged from the air outlet 23 parallel to the concentrator 10's axis A in the form of a primary airflow discharge jet whose cross-section may broaden relatively slowly as it flows away from the concentrator 10.

It has been discovered that by discharging the primary airflow 103 in the form of a jet, by orienting the primary airflow discharge jet so that it flows away from the fan assembly 11 along the concentrator 10's axis A, and by constructing the concentrator 10 so that the sampled airflow 102 flows radially inwardly towards its axis A as the sampled airflow 102 enters the air processor 12, any mixing of the primary airflow discharge jet with the incoming sampled airflow 102 will tend to be desirably minimized. Minimizing such mixing may be desirable because many of the particles containing target material will have been removed from the sampled airflow 102 as it flows through the assembly 12. Thus, the depleted primary airflow 103 discharged from the fan assembly 11 will contain relatively few remaining particles containing target material. As a result, if the depleted primary airflow 103 is mixed with the incoming sampled airflow 102, the depleted primary airflow 103 will tend to undesirably reduce, or dilute, the concentration of the particles containing target material in the incoming sampled airflow 102.

In addition, it has been further discovered that the primary airflow discharge jet from the plenum 15 may desirably generate an induced draft effect around the concentrator 10. An induced draft effect is where the primary airflow discharge jet will entrain some of the air surrounding the concentrator 10, thereby causing a desirable radially inward flow towards the air processor 12. It has been further discovered that in a situation where the sampled air around the concentrator 10 is stagnant, this induced draft effect may desirably cause the circular sensing radius of the concentrator 10 to more than double.

The concentrator 10's circular sensing radius may be defined as the maximum radius around the concentrator 10 from which it will take a predetermined amount of time for sampled air to be drawn into the air processor 12. For example, if the predetermined amount of time is five minutes, then the circular sensing radius will be eight feet if it took five minutes for air that was formerly eight feet away from the air processor 12 to be drawn into the air processor 12. It is apparent that doubling the concentrator 10's circular sensing radius may be highly desirable, such as in a circumstance where the particles containing target material are not uniformly distributed through the air surrounding the concentrator 10.

However, as an alternative, the fan assembly 11 may be modified in any suitable way so that the discharged primary airflow 103 is discharged from the plenum 15 in any desired direction, either in the form of a jet, or not in the form of a jet.

The Air Processor 12

Figure 4:
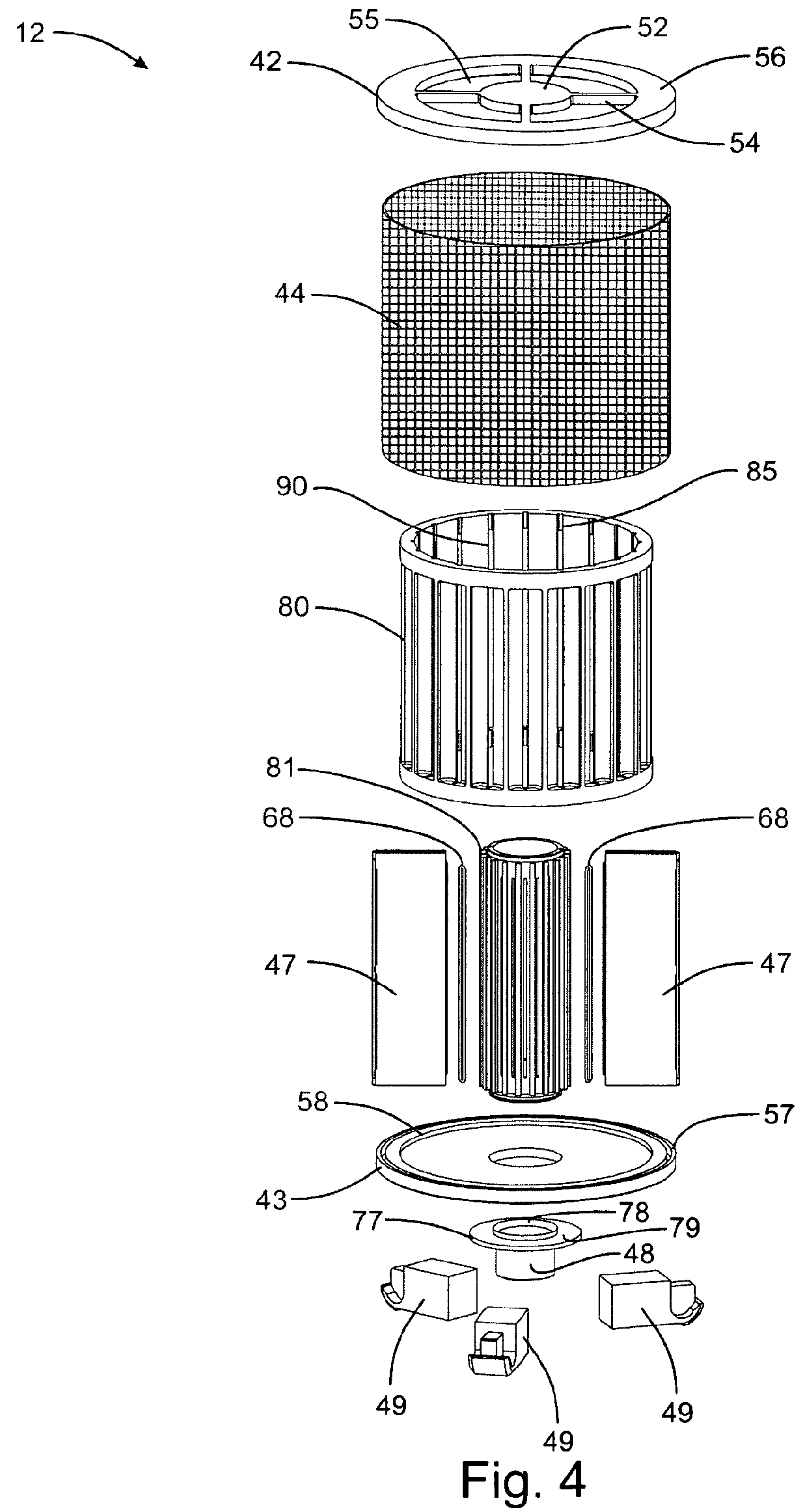
FIG. 4 is an exploded perspective view of the concentrator 10's air processor 12, taken from an upper aspect.

As best seen in FIGS. 1-2 and 4, the air processor 12 may comprise top and bottom end plates 42, 43, a hollow outer hub 80, a hollow inner hub 81, and blades 47.

Although the hubs 80, 81 are illustrated as having generally circular cross-sectional profiles of constant size and shape along their respective lengths, either or both may have any other suitable geometric or non-geometric cross-sectional profiles, and their respective cross-sectional areas and shapes may not be constant along their respective lengths.

O-rings 68 may be provided for the blades 47, and an O-ring 101 may be provided for the neck 99 of the inner hub 81. The O-rings 68, 101 may, or may not, comprise part of the air processor 12.

An annular filter 44 may be provided to prevent anything that is significantly larger than a predetermined size from entering the outer hub 80, to help prevent foreign matter and debris from entering the outer hub 80. For example, the filter 44 may be selected to prevent the entry of anything that is significantly larger than the particles containing target material. The filter 44 may, or may not, comprise part of the air processor 12.

Figure 7:
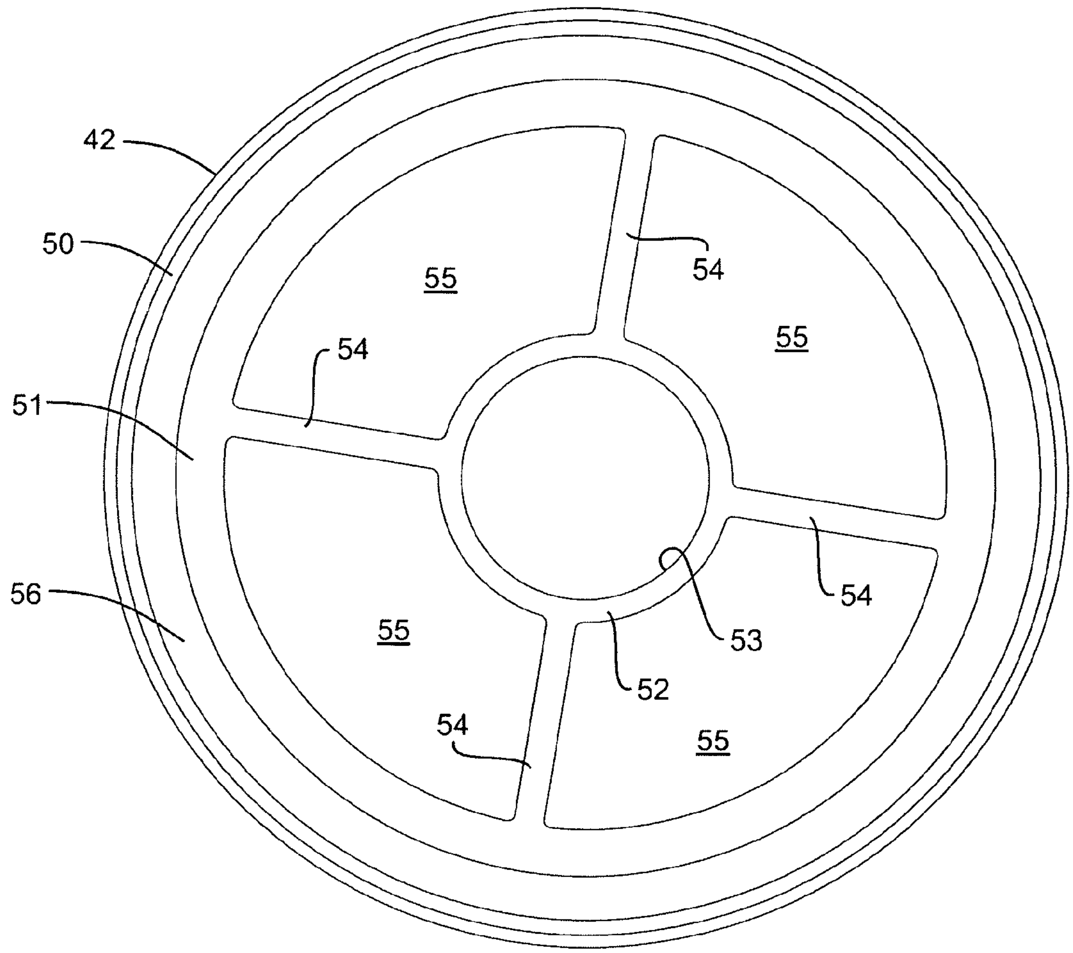
FIG. 7 is a bottom plan view of the air processor 12's top plate 42.
Figure 10:
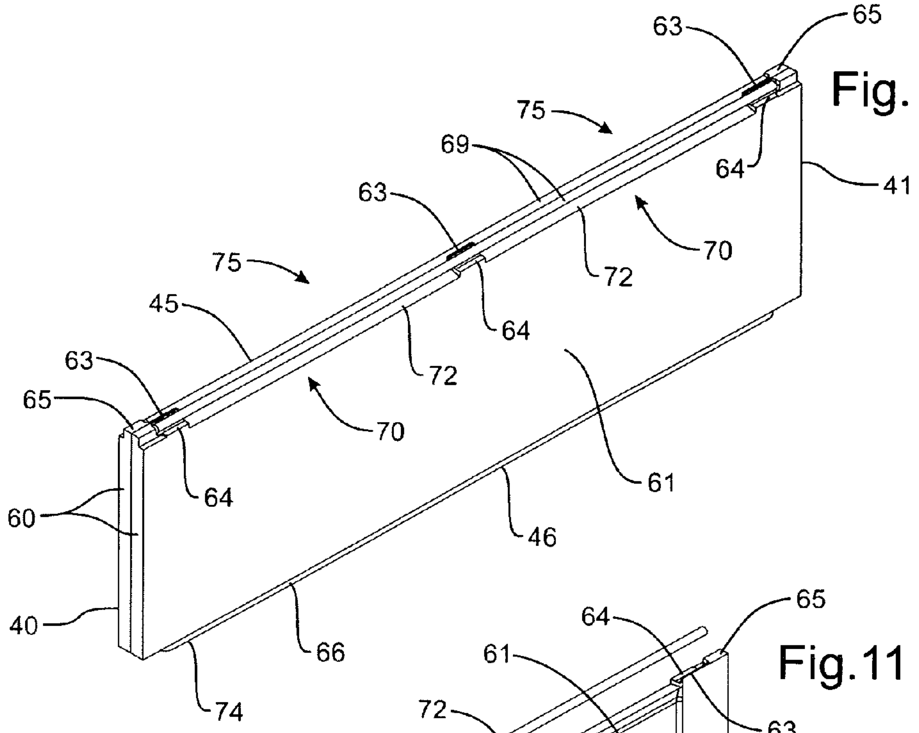
FIG. 10 is a perspective view of one of the air processor 12's blades 47.
Figure 11:
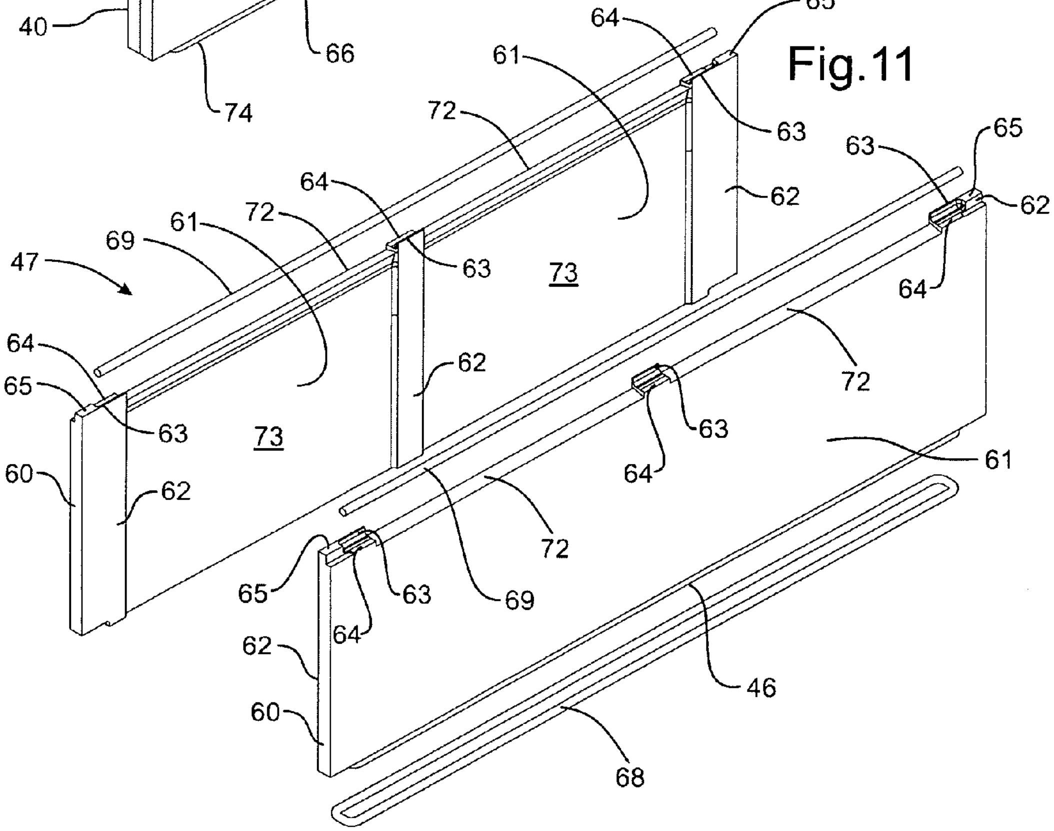
FIG. 11 is an exploded perspective view of one of the air processor 12's blades 47.
Figure 12A:
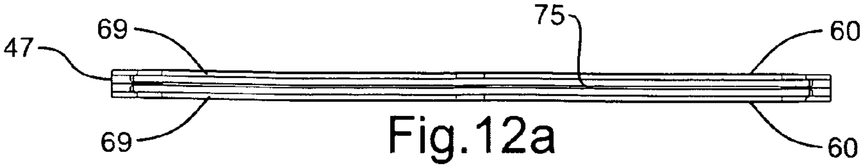
FIG. 12*a* is a top plan view of one of the air processor 12's blades 47.
Figure 12:
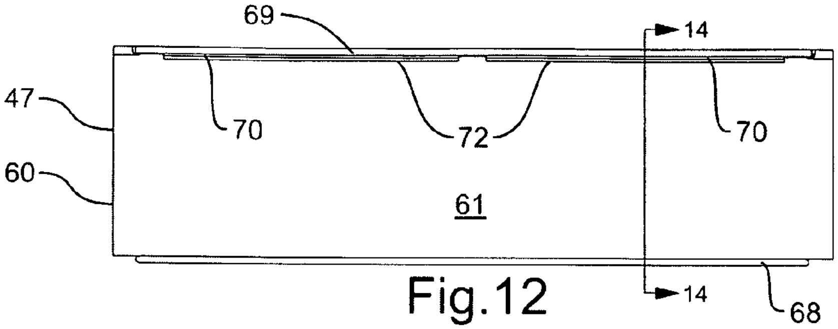
FIG. 12 is a side elevational view of one of the air processor 12's blades 47.
Figure 12B:
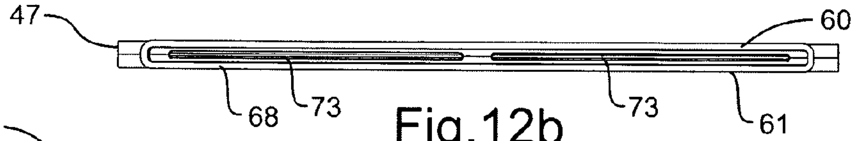
FIG. 12*b* is a bottom plan view of one of the air processor 12's blades 47.
Figure 13:
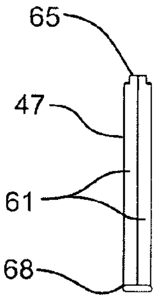
FIG. 13 is an end elevational view of one of the air processor 12's blades 47.
Figure 14:
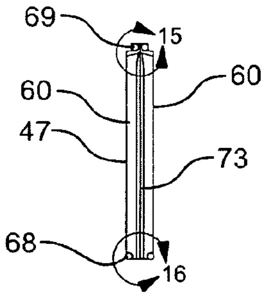
FIG. 14 is a cross-sectional view of one of the air processor 12's blades 47, taken along line 14-14 of FIG. 12.

As best seen in FIGS. 2, 4 and 7, the top plate 42 may have a rim 56, a center plate 52 connected to the rim 56 by four arms 54, and four primary airflow outlets 55. The rim 56 may have an annular groove 50 for receiving the top edge of the filter 44, and an annular recess 51 for receiving the top end of the outer hub 80. The center plate 52 may define a circular recess 53 for receiving the top neck 98 of the inner hub 81.

As best seen in FIGS. 2 and 4, the bottom plate 43 may have an annular groove 57 for receiving the bottom edge of the filter 44, an annular recess 58 for receiving the bottom end of the outer hub 80, and an opening 59 for receiving the bottom neck 99 of the inner hub 81.

The Blades 47

Turning now to FIGS. 2, 4, 5-6 and 10-16, each blade 47 may be symmetrical about an imaginary plane of symmetry that passes longitudinally through the center of the blade 47; and may comprise a pair of identical blade elements 60. Alternatively, each blade 47 may not be symmetrical about such a plane, and the blade elements 60 may not be identical.

Each blade element 60 may comprise a blade body 61; a rod 69; three secondary airflow channel spacers 62; three sampled airflow inlet spacers 63; three primary airflow outlet spacers 64; a pair of optional blade mounting flanges 65; an O-ring mounting flange 66 having a groove 67 for an O-ring 68; and a pair of outer edges 72 that extend between respective adjacent pairs of the primary airflow outlet spacers 64.

As best seen in FIGS. 5-6 and 10-16, a blade 47 may have a pair of sampled airflow inlet ports 75 that may be formed by its pair of cylindrical rods 69. Cylindrical rods 69 are a preferred method for creating the sampled airflow inlet ports 75 because they may provide a wide range of useful naturally converging-diverging nozzle profiles for the sampled airflow inlet ports 75, and because rods 69 are commercially available at low cost in a wide variety of sizes, made from many different materials and available with extremely high quality surface finishes. Smaller diameter rods 69 may also be called 'wires' in commerce, but no such distinction is recognized herein. Alternatively, the inlet ports 75 may be formed in any other suitable way by any other suitable structure, such being formed by the outer hub 80 (in which case the rods 69 may be eliminated), or by any suitable combination of partly being formed by the rods 69, and partly being formed by the outer hub 80.

By way of example, the sampled airflow inlet ports 75 will be described and illustrated as being sampled airflow inlet slots 75, it being understood that the inlet ports 75 may have any other suitable size, shape and construction; and that the same, or similar, disclosures made herein regarding the inlet slots 75 may apply equally well, wholly or in part, to an inlet port 75 that is not an inlet slot 75.

Figure 6:
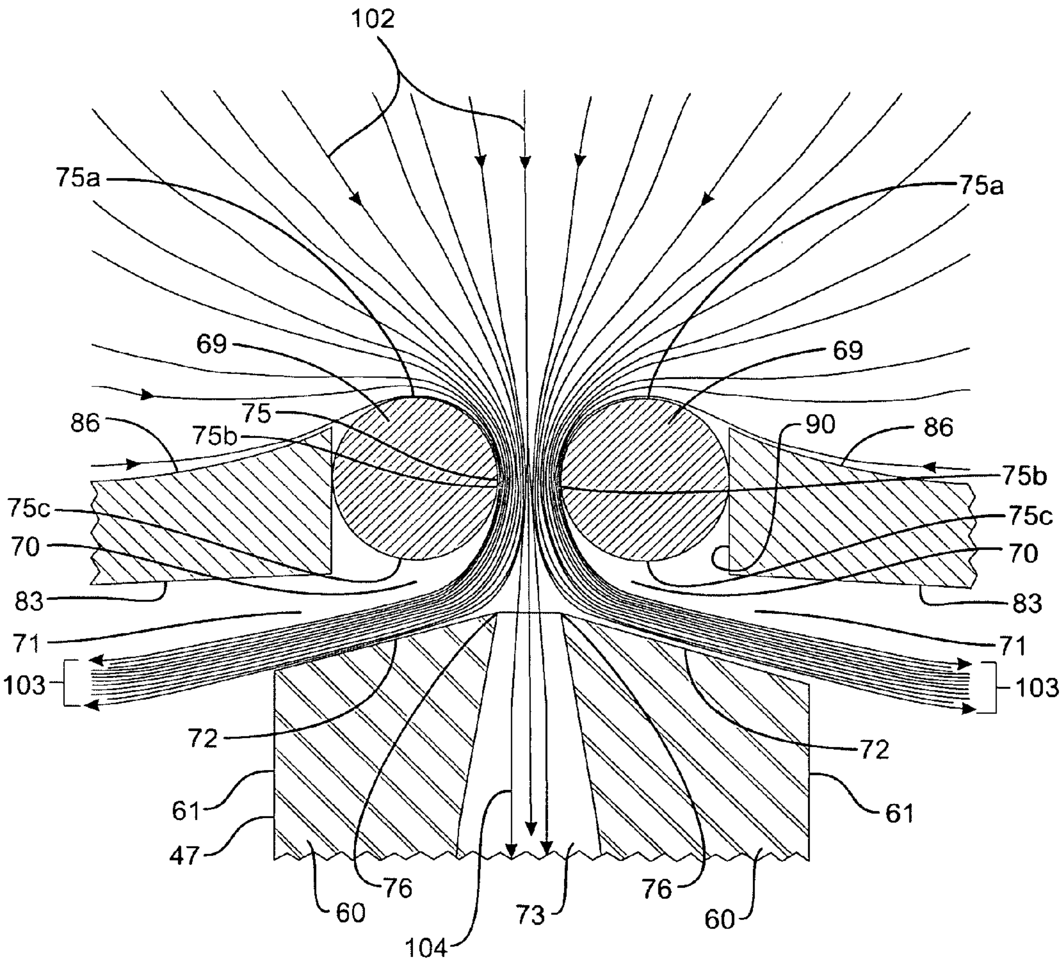
FIG. 6 is an enlarged view similar to that of FIG. 5A, but with airflow lines added to show sampled airflows 102, primary airflows 103 and secondary airflows 104.

As best seen in FIG. 6, the sides of an inlet slot 75, from its upstream side **75*a*, to its through stream side 75*b*, to its downstream side 75*c*, may have a circular cross-sectional profile due to the cylindrical nature of the rods 69. Alternatively, the rods 69 and the sides 75*a*-75*c* of the inlet slots 75 may have any other suitable smoothly varying, arcuate profile other than circular, such as oval, elliptical or parabolic. As a further alternative, rods 69 and the sides 75*a*-75*c* of the inlet slots 75 may have any other suitable geometric, or non-geometric cross-sectional profile. In addition, the arcuate length of the upstream and downstream sides 75*a*, 75*c*** may be shorter, or longer, than that which is illustrated.

The width of an inlet slot 75 may be equal to the minimum distance between the rods 69 (i.e., may be equal to the combined thicknesses of a facing pair of the sampled airflow inlet spacers 63), and the length of an inlet slot 75 may be equal to the distance between its adjacent pairs of spacers 63.

Each blade element 60 may have a pair of primary airflow outlet ports 70 that may be defined between its rods 69 and the blade element 60's outer edges 72. Alternatively, the outlet ports 70 may be formed in any other suitable way by any other suitable structure, such by being formed by the outer hub 80 (in which case the rods 69 may be eliminated), or by any suitable combination of partly being formed by the rods 69, partly being formed by the outer hub 80, and partly being formed by the outer edges 72.

By way of example, the primary airflow outlet ports 70 will be described and illustrated as being primary airflow outlet slots 70, it being understood that the outlet ports 70 may have any other suitable size, shape and construction; and that the same, or similar, disclosures made herein regarding the outlet slots 70 may apply equally well, wholly or in part, to an outlet port 70 that is not an outlet slot 70.

As best seen in FIG. 6, the upper side of the outlet slot 70 (the downstream side **75*c* of the rod 69) may have a circular cross-sectional profile due to the cylindrical nature of the rod 69. Alternatively, the upper side of the outlet slot 70 may have any other suitable curved (such as oval, elliptical or parabolic), geometric, or non-geometric cross-sectional profile. In addition, the arcuate length of the upper side of the outlet slot 70** may be may be shorter, or longer, than that which is illustrated.

Although the lower side of the outlet slot 70, i.e., the outer edge 72 of the blade 47, is illustrated as having a flat cross-sectional profile, it may have any other suitable curved, geometric or non-geometric cross-sectional profile.

In addition, the plane of each edge 72 may lie at an inside angle of about 75 degrees with respect to an imaginary plane of symmetry that passes longitudinally through the center of the blade 47 and that bisects the blade 47 into two identical blade elements 60. It has been discovered that good flow of the primary airflow 103 through the primary airflow slots 70 may be achieved if the inside angle is in the range of from about 70 degrees to about 80 degrees, although the inside angle may be less than 70 degrees or greater than 80 degrees. A preferred inside angle may be about 75 degrees.

The width of a primary airflow outlet slot 70 (i.e., the minimum distance between its rod 69 and its outer edge 72) may be about the same as the thickness of its adjacent primary airflow outlet spacers 64 (i.e., the distance the spacers 64 extend outwardly past the outer edge 72), and its length may be equal to the distance between its adjacent primary airflow outlet spacers 64.

A blade 47 may also have a pair of secondary airflow inlet ports 76 that may be formed by the inner edges 72 of its blade bodies 61. Alternatively, the inlet ports 76 may be formed in any other suitable way by any other suitable structure, such being formed by the outer hub 80, or by any suitable combination of partly being formed by the outer hub 80 and partly being formed by any suitably sized and shaped part of the blade bodies 61.

By way of example, the secondary airflow inlet ports 76 will be described and illustrated as being knife-edged secondary airflow inlet slots 76 that are formed by the inner edges 72 of the blade bodies 61, it being understood that the inlet slots 76 may have any other suitable size, shape and construction; and that the same, or similar, disclosures made herein regarding the inlet slots 76 may apply equally well, wholly or in part, to an inlet port 76 that is not an inlet slot 76.

Although both sides of the inlet slot 76 are illustrated as being knife-edged, as an alternative only one side of the inlet slot 76 may be knife edged. As further alternatives, the inlet slot 76 may be provided with any other suitable knife-edges of any suitable size, shape and construction other than those illustrated, such knife-edges that extend upwardly towards the sampled airflow inlet slot 75 (i.e., towards the downstream side of the inlet slot 75), for any suitable distance into the sampled airflow 102 that exits from the sampled airflow inlet slot 75.

As best seen in FIG. 6, the sides of an inlet slot 75, from its upstream side 75*a*, to its through stream side 75*b*, to its downstream side 75*c*, may have a circular cross-sectional profile due to the cylindrical nature of the rods 69. Alternatively, the sides 75*a*-75*c* of the inlet slots 75 may have any other suitable curved (such as oval, elliptical or parabolic), geometric, or non-geometric cross-sectional profile. In addition, the arcuate length of the upstream and downstream sides 75*a*, 75*c* may be shorter, or longer, than that which is illustrated.

Each of a blade 47's secondary airflow inlet slots 76 may comprise a secondary airflow channel 73 that is located between its blade bodies 61. Two of the sides of each channel 73 may be formed by its adjacent pairs of secondary airflow channel spacers 62, while its other two sides may be formed by the corresponding facing portions of its blade bodies 61.

The width of a secondary airflow channel 73 may be equal to the distance between the corresponding facing portions of its blade bodies 61, its height may be equal to the distance between its respective adjacent pairs of the secondary airflow channel spacers 62; and its length may be equal to the distance between its secondary airflow inlet slot 76 and its secondary airflow outlet slot 105.

Figure 17:
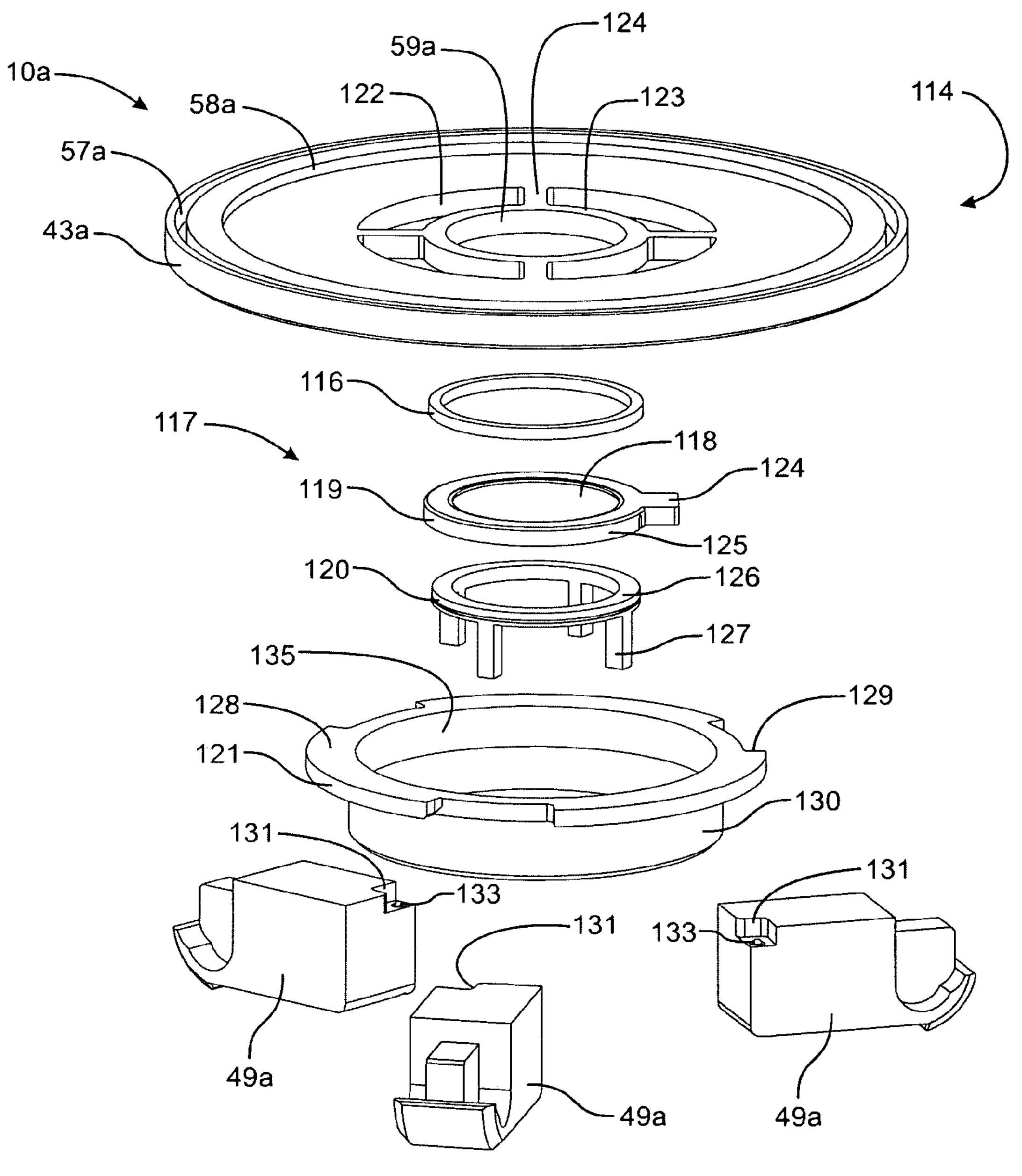
FIG. 17 is an exploded perspective view of the lower portion of a concentrator 10*a*, taken from an upper aspect.
Figure 18:
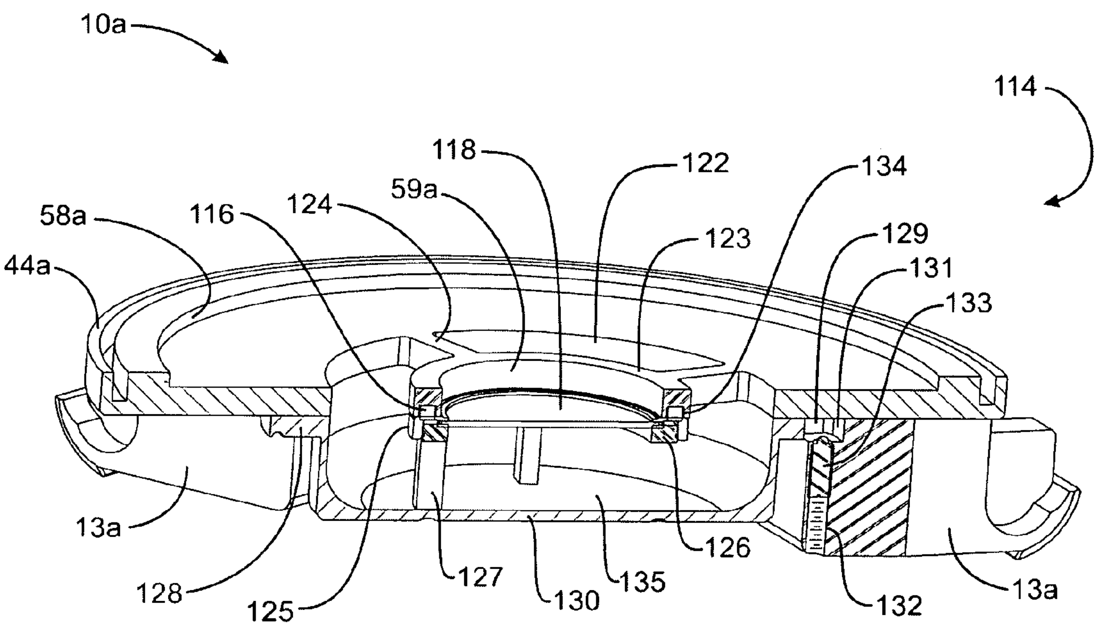
FIG. 18 is an assembled perspective view, partly in cross-section, of the lower portion of a concentrator 10*a*, taken from an upper aspect.
Figure 19:
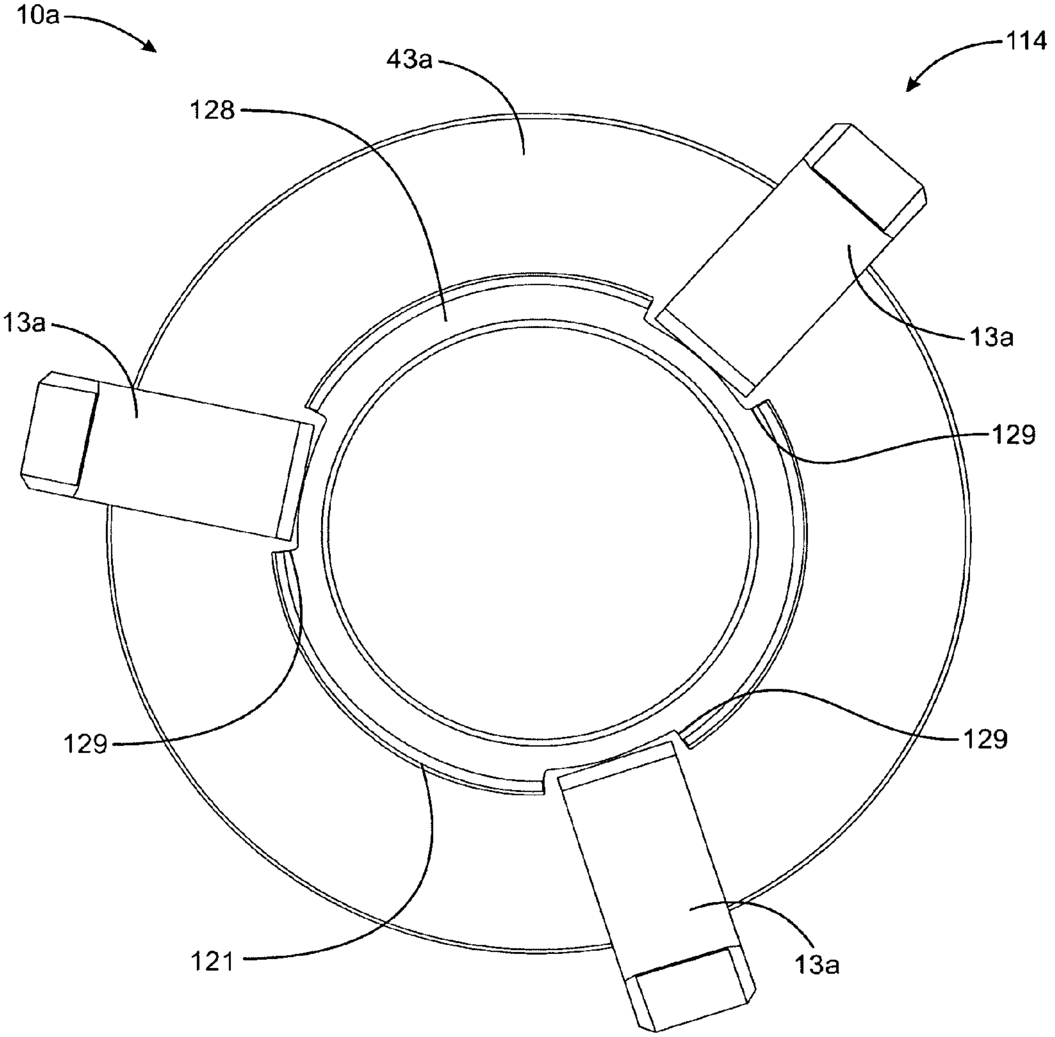
FIG. 19 is a bottom plan view of the concentrator 10*a;*

The width of a secondary airflow channel 73 may gradually increase for a short distance downstream from its inlet slot 76, and then stay at this increased width for the remainder of the length of the channel 73. This may be done in order to convert some of the kinetic energy of the high velocity secondary airflow 104 that enters through the secondary airflow inlet slot 76 into static pressure, so that the air pressure of the secondary airflow 104 within the channel 73 may be closer to the ambient pressure of the sampled air at the outer hub 80's sampled airflow inlet pockets 84, than would otherwise be the case. This "pressure recovery" effect may be useful because, for example: (a) it may desirably reduce the amount of suction that may be required by a downstream air sampler, particle analyzer, or analytical device that may be connected to the air processor 12's outlet fitting 77; and (b) it may desirably help permit the concentrator 10*a* that is illustrated in FIGS. 17-19 to be operated as a stand-alone, high-volume, filter-based air sampler.

As an alternative, there may be as few as two, or more than three, of the sampled airflow inlet spacers 63, primary airflow outlet spacers 64, and secondary airflow channel spacers 62, respectively; in which case the number of sampled airflow inlet slots 75, primary airflow outlet slots 70, secondary airflow inlet slots 76, and secondary airflow channels 73 of a blade 47 may decrease or increase accordingly.

As best seen in FIG. 6, when a blade 47 is installed in the outer hub 80 the primary airflow slot 70 may comprise a downstream, primary airflow channel 71 that may be formed between a portion of each edge 72 of the blade 47 and the inner surface 83 of the outer hub 80. As is also best seen in FIG. 6, the plane of each edge 72 may lie at an inside angle of about 75 degrees with respect to an imaginary plane of symmetry that passes longitudinally through the center of the blade 47 and that bisects the blade 47 into two identical blade elements 60. It has been discovered that good flow of the primary airflow 103 through the primary airflow channels 71 may be achieved if the inside angle is in the range of from about 70 degrees to about 80 degrees, although the inside angle may be less than 70 degrees or greater than 80 degrees. A preferred inside angle may be about 75 degrees.

A blade 47 may be assembled in any suitable way, such as by assembling its rods 69 to its spacers 63, 64, and by then assembling together its two blade elements 60. Any suitable means may be used to assemble a blade 47, such as by using fasteners; interference fits; friction fits; barbed, threaded, bonded, glued or welded connections; splines; keys; or mechanical couplers.

When a blade 47 has been assembled, there may be a fluid-tight seal between the corresponding contacting surfaces of the secondary airflow channel spacers 62 and sampled airflow inlet spacers 63 of its two blade elements 60.

Each blade 47 may have corresponding respective parts in the outer and inner hubs 80, 81, namely: (a) a mounting slot 85, a sampled airflow inlet pocket 84, and a sampled airflow inlet slot 90 in the outer hub 80; and (b) a mounting slot 94 and a secondary airflow inlet slot 96 in the inner hub 81. Although twenty blades 47 (and their corresponding respective parts) are illustrated, there may be as few as one blade 47 (and its corresponding respective parts), or there may be more than twenty blades 47 (and their corresponding respective parts). Each blade 47 (and its corresponding respective parts) may, or may not, be the same as the other blades 47 (and their corresponding respective parts), such as with respect to their size, shape, construction and air handling capacity.

Each blade 47 may be flat as illustrated, or it may be curved, bowed or twisted between its air inlet and air outlet sides 45, 46 and between its top and bottom sides 40, 41.

Although the blade 47's sampled airflow inlet slots 75, primary airflow outlet slots 70, and secondary airflow inlet slots 76 are illustrated as being straight, and as having a constant size and shape along their respective lengths, they may not be straight, and they may not have a constant size and shape along their lengths.

Although the blade 47's rods 69 are illustrated as being straight, and as having a circular cross-sectional profile that is constant in size and shape along their lengths, they may not be straight, they may have any other suitable geometric or non-geometric cross-sectional profile, and they may not have a constant size and shape along their lengths. In addition, all of the rods 69 may, or may not, be the same in all respects.

The Outer and Inner Hubs 80, 81

As best seen in FIGS. 2, 4-6, 8, and 8A, the hollow outer hub 80 may have top and bottom ends 87, 88; a sidewall 89; and a central cavity 97. The outer hub 80 may also have for each blade 47 a respective hub sampled airflow inlet port of any suitable size, shape and construction. For example a hub sampled airflow inlet port may comprise an elongated sampled airflow inlet pocket 84 in the outer surface 82 of its sidewall 89, and a respective elongated mounting slot 85 in the inner surface 83 of its sidewall 89 for receiving the mounting flanges 65 of its respective blade 47.

Each mounting slot 85 may extend from the hub 80's top end 87 to its bottom end 88. An elongated central portion of each mounting slot 85 may form a sampled airflow inlet slot 90 that is in fluid communication with a respective sampled airflow inlet pocket 84. The inlet slot 90 and inlet pocket 84 may have a length sufficient to make them operable to convey a sampled airflow 102 to the sampled airflow inlet slots 75 of their respective blade 47.

A sampled airflow inlet pocket 84 may comprise two concave sampled airflow inlet lobes 86, one on either side of the sampled airflow inlet slot 90. Although the lateral sides of the pocket 84 and lobes 86 are illustrated as having an arcuate profile of constant size and shape along their lengths, they may have any other suitable profile, and may not be of constant size and shape along their lengths. As an alternative, the sampled airflow inlet pocket 84, or one or both of its lobes 86 may be eliminated.

As best seen in FIGS. 2, 4-5, 9, and 9A, the hollow inner hub 81 may have top and bottom ends 91, 92, a sidewall 93 and a central cavity 95. The inner hub 81 may have for each blade 47 a respective elongated mounting slot 94 in the outer surface of its sidewall 93 for receiving the O-ring mounting flange 66 and O-ring 68 of a respective blade 47. The mounting slot 94 may extend from the hub 81's top end 91 to its bottom end 92. A portion of the mounting slot 94 may form a secondary airflow inlet port 96 for the inner hub 81 that is in fluid communication with the central cavity 95. The secondary airflow inlet port 96 may have any suitable size, shape and construction. For example, the secondary airflow inlet port 96 may be a secondary airflow inlet slot 96. The inlet slot 96 may have a length sufficient to make it operable to receive a secondary airflow 104 from the secondary airflow outlet slots 105 of its respective blade 47. The width of the inlet slot 96 may be selected to be at least as large as the width of its corresponding outlet slots 105, although its width may be selected to be greater or lesser.

The inner hub 81's top end 91 may have a neck 98 that is sized to be received by the recess 53 in the top plate 42 of the air processor 12. The inner hub 81's bottom end 92 may have a hollow neck 99 having a groove 100 for an O-ring 101. The hollow neck 99 may serve as a secondary airflow outlet 99 for the inner hub 81 and may be sized to be received by the opening 59 in the bottom plate 43 of the assembly 12.

The air processor 12 may further comprise an optional outlet fitting 77 having a neck 78 sized to fit within the bottom end 92 of the hub 81, and a flange 79 that is larger than the opening 59 in the bottom plate 43 of the assembly 12.

Although the outer and inner hubs 80, 81 are illustrated as generally being elongated cylinders that are straight along their lengths, either or both of them may not generally be an elongated cylinder, and may not be straight. Although their central cavities 97, 95 are illustrated as having circular cross-sectional profiles of constant size and shape along their lengths, their central cavities 97, 95 may not have a cross-sectional profile of constant size and shape along their lengths, and may have any other suitable geometric or non-geometric cross-sectional profile. The size, shape and construction of the top and bottom plates 42, 43, may be modified in any suitable way so as to be operable with any outer and inner hubs 80, 81 of any given size shape and construction.

Although the sampled airflow inlet slots 90, and the secondary airflow inlet slots 96 are illustrated as being straight and as having a constant size and shape along their lengths, they may not be straight and may not have a constant size and shape along their lengths.

Assembly of the Air Processor 12

The air processor 12 may be assembled in any suitable way, such as by placing the bottom edge of the annular filter 44 in its mounting groove 57 in the bottom plate 43, and by placing the bottom end 88 of the outer hub 80 in its recess 58 in the bottom plate 43. There may be a fluid-tight seal between the bottom plate 43 on the one hand, and the bottom end 88 of the outer hub 80 and the bottom edge of the filter 44 on the other hand.

The O-ring 101 may be assembled to the neck 99 of the inner hub 81, by seating it in its groove 100 on the neck 99. The neck 99, with its O-ring 101, may then be inserted into the opening 59 in the bottom plate 43. The O-ring 101 may provide a fluid-tight seal between the neck 99 and the opening 59.

Each blade 47 may have its O-ring 68 assembled to its O-ring mounting flanges 66 by seating the O-ring 68 in the grooves 67 in its flanges 66. Each blade 47 may then be inserted into its respective mounting slots 85, 94 in the outer and inner hubs 80, 81 until it is in contact with the bottom plate 43.

Figure 5:
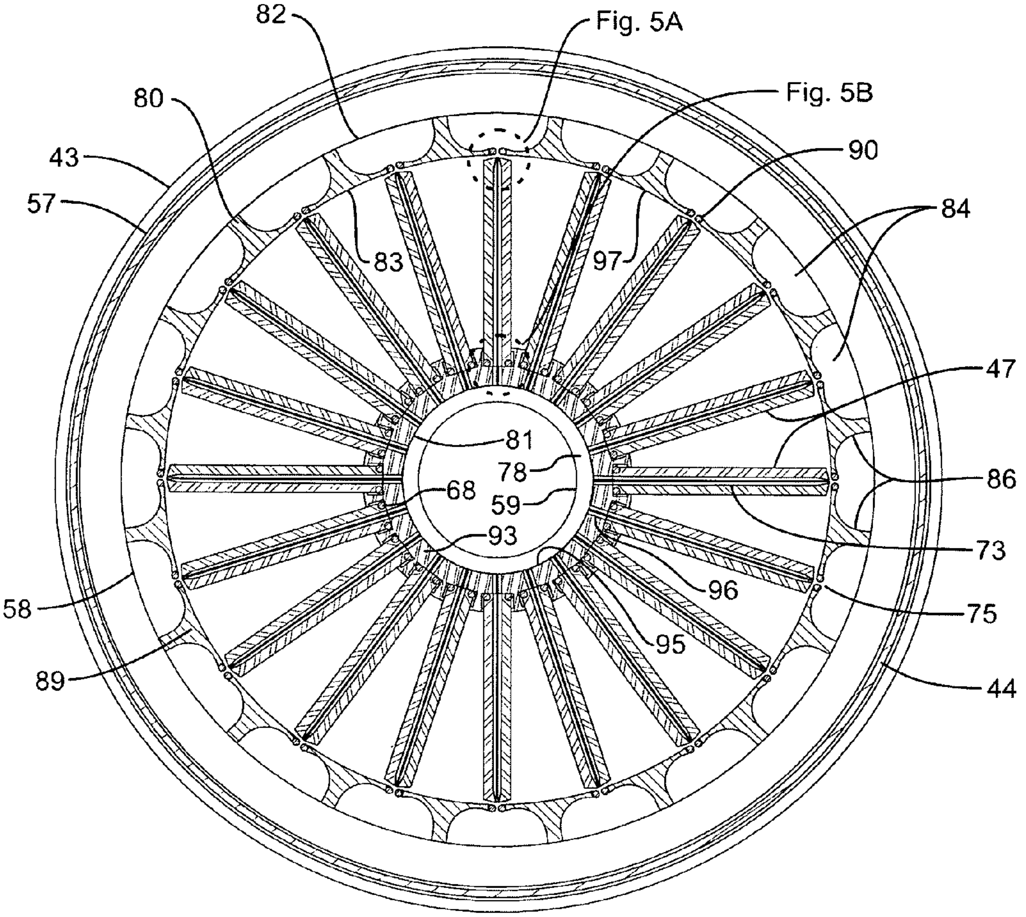
FIG. 5 is a cross-sectional view of the concentrator 10's air processor 12, taken along line 5-5 of FIG. 1.

The O-ring 68 may serve multiple functions. As best seen in FIGS. 5 and 5B, the O-ring 68 may provide a fluid-tight seal between the blade 47 and its mounting slot 94 in the inner hub 81. In addition, the O-ring 68 may also serve the function of resiliently urging its blade 47 radially outwardly, to properly seat its blade 47 in its respective mounting slot 85 in the outer hub 80. This may provide the dual functions of: (a) helping to provide a fluid-tight seal between the mounting flanges 65 of its blade 47 and its respective mounting slot 85, and (b) helping to properly locate the blade 47's sampled airflow inlet slot 75 with respect to its respective sampled airflow inlet slot 90 in the outer hub 80.

The top plate 42 may then be assembled to the filter 44, outer hub 80, and inner hub 81 by inserting the top edge of the filter 44 into its annular groove 50 in the top plate 42, by inserting the top end 87 of the outer hub 80 into its annular recess 51 in the top plate 42, and by inserting the top neck 98 of the inner hub 81 into its circular recess 53 in the top plate 42. Fluid-tight seals may be provided between the top plate 42 on one hand, and the top end 87 of the outer hub 80, the neck 98 of the inner hub 81, and the top edge of the filter 44 on the other hand.

The optional mounting feet 49 for the optional tripod legs 13 may be assembled to the bottom plate 43 in any suitable location on the bottom plate 43. The legs 13 may then be assembled to their respective mounting feet 49. The mounting feet 49 and legs 13 may, or may not, comprise part of the air processor 12.

It may be preferable that subsequent access to the interior of air processor 12, such as for cleaning, be performed by removing bottom plate 43, rather than top plate 42. This is because it may be difficult to access the connection between fan assembly 11 and air processor 12, once the fan 16, fan plate 18 and vanes 19 have been assembled to the fan plenum 15.

The fan assembly 11 and the air processor 12 may be assembled together by assembling the mounting flange 25 of the fan assembly 11 to the top surface of the top plate 43 of the air processor 12. A fluid-tight seal may be provided between the mounting flange 25 and the top plate 43.

An optional outlet fitting 77, which may or may not comprise part of the air processor 12, may be assembled to the bottom plate 43 by inserting its top neck 78 into the secondary airflow outlet 99 of the inner hub 81 until its flange 79 is in contact with the bottom of the bottom plate 43. Fluid-tight seals may be provided between its neck 78 and the inner hub 81, and between its flange 79 and the bottom plate 43. The air input of any suitable air sampler, particle analyzer, or analytical device which may or may not comprise part of the air processor 12, may then be connected in any suitable way to the bottom neck 48 of the outlet fitting 77 either directly, or indirectly, so that it can receive the secondary airflow 104 and the particles containing target material that it contains from the inner hub 81.

Alternatively, any other suitable outlet fitting 77 may be provided which is operable to serve the functions of the outlet fitting 77. As a further alternative, the outlet fitting 77 may be eliminated and the air input of the air sampler, particle analyzer, or analytical device may be connected in any suitable way to the secondary airflow outlet 99 of the inner hub 81, either directly or indirectly.

The various parts of the concentrator 10 may be assembled together in any suitable ways, such by using fasteners; interference fits, friction fits; barbed, threaded, bonded, glued or welded connections; splines; keys; or mechanical couplers.

The O-rings 68 and 101 may be made from rubber or any other suitable resilient or elastomeric material. The filter 44 may be made from any suitable screening or from any suitable filter media, depending on the size of the undesired particles that it is designed to prevent from entering the outer hub 80.

The fan assembly 11's plenum 15, fan plate 18, impeller 30, and vanes 19; the power cable assembly 21's conduit 35, connector 37, and clips 38, 39; and the air processor 12's top and bottom plates 42, 43, outer and inner hubs 80, 81, and blades 47 may be made in any suitable way from any suitable strong, durable substance, such as from metal, plastic, or composite material.

Operation of the Air Processor 12

In order to create a sampled airflow 102 that flows into the air processor 12, the fan 16 in the fan assembly 11 may be turned on, to create a negative air pressure in the air outlets 55 in the top plate 42 and in the cavity 97 of the outer hub 80. The higher ambient pressure sampled air in the vicinity of the inlet pockets 84 and inlet slots 90 of the outer hub 80 may then create a sampled airflow 102 that flows into the pockets 84, whose curved, concave lobes 86 may desirably impart some rotational motion to the sampled airflow 102 within the pockets 84 before it reaches the inlet slots 90.

For simplicity, and referring now to FIG. 6, the flow of the sampled airflow 102 through one pocket 84 and its respective inlet slot 90 and blade 47 will now be described, it being understood that similar comments may apply to the flow of the sampled airflow 102 into the other pockets 84, inlet slots 90 and their respective blades 47. In addition, the flow of the sampled airflow 102 through only one of the blade 47's sampled airflow inlet slots 75 will be described, it being understood that similar comments may apply to the other of its inlet slots 75.

The sampled airflow 102 from the inlet slot 90 may enter the blade 47 through the sampled airflow inlet slot 75 that is created by its rods 69. As best seen in FIG. 6, the circular profiles of the blade 47's rods 69 may force the incoming sampled airflow 102 into two mirror image semicircular flow patterns around the rods 69 relative to an imaginary plane of symmetry that passes longitudinally through the center of the blade 47 and through the center of its sampled airflow inlet slot 75.

The rotation of the two semicircular flow patterns of the sampled airflow 102 as they flow around their respective rods 69 causes the particles containing target material in the sampled airflow 102 to be subjected to strong centrifugal forces that urge the particles containing target material to move towards the imaginary plane of symmetry, thereby concentrating the particles containing target material in the central portion of the sampled airflow 102 as it passes through the sampled airflow inlet slot 75 that is formed by the rods 69.

The blade 47's knife-edged secondary airflow inlet slot 76 may then divide the sampled airflow 102 that it receives from the sampled airflow inlet slot 75 into: (a) left and right primary airflows 103 that flow through the left and right primary airflow slots 70 of the blade 47 and into the left and right primary airflow channels 71 between the outer edges 72 of the blades 47 and the inner surface 83 of the outer hub 80, and (b) one central secondary airflow 104 that passes into the secondary airflow channel 73 within the blade 47.

The rotation of the sampled airflow 102 around the downstream surfaces of the rods 69 as the sampled airflow 102 is divided into the left and right primary airflows 103 by the inlet slot 76 causes particles containing target material in the sampled airflow 102 to be further subjected to strong centrifugal forces that also urge the particles containing target material to move towards the imaginary plane of symmetry, thereby further concentrating the particles containing target material in the central portion of the sampled airflow 102 downstream from the sampled airflow inlet slot 75 that is formed by the rods 69.

The primary airflows 103 from all of the blades 47 enter the central cavity 97 in the outer hub 80 between the blades 47, and exit the central cavity 97 through the primary airflow outlets 55 in the top plate 42.

The secondary airflow 104 that passes into the secondary airflow channel 73 within the blade 47 carries concentrated particles containing target material because it was created from the central portion of the sampled airflow 102 where the particles containing target material were concentrated, while the left and right primary airflows 103 carry relatively few particles containing target material since they received sampled air from the left and right sides of the sampled airflow 102 which carried relatively few particles containing target material after passing through the inlet slot 75.

Many conventional concentrators rely on virtual impaction principles. Incoming air is prepared for the impaction process by first being formed into a very well-defined collimated beam of air, which is also commonly referred to as a jet of air. Collimation of the primary beam is done by using a very gradually tapered primary slit, or a short straight slit section placed immediately before the point where the beam exits the primary collimating structure.

Once the beam of air issues out of the primary slit, it flows across a gap and impinges on a secondary surface containing a second slit. The surface the secondary slit is contained within may range from two angled thin plates, to a flat plane. On the order of 10% of the incoming air jet is taken into the secondary slit, while 45% is exhausted to each side of the slit. The momentum of particulates in the primary beam, assisted by the secondary airflow, causes a fraction of the particulates in the primary beam to penetrate into the secondary slit, instead of continuing on in the sharply deflected and bifurcated primary beam paths. Particulates trapped by the secondary airflow appear as a concentrate of particles therein. This process is very energy inefficient, and frictional losses and geometric expansion losses create a large pressure drop across the primary air circuit.

It has been discovered that a significant portion of this undesirable pressure drop can be circumvented by the concentrator 10's air processor 12, because it does not convert the incoming sampled airflow 102 into a collimated beam of sample air. Instead, the sampled airflow 102 flows towards, and through the sampled airflow inlet ports 75 as a non-collimated sampled airflow 102.

The sampled airflow 102 is received by the air processor 12's sampled airflow inlet ports 75 which, as best seen in FIG. 6, form a two-dimensional contracting/expanding nozzle profile that subjects the sampled airflow 102 to significant centrifugal forces that move particles containing target material towards the central portion of the sampled airflow 102 even before the sampled airflow 102 arrives at the narrowest part of the sampled airflow inlet ports 75. By placing the secondary airflow inlet ports 76 at a location that is appropriately close to the downstream side of their respective sampled airflow inlet ports 75 and by properly shaping the profiles of the inlet ports 75, the pressure drop that would otherwise be associated with the sampled airflow 102 entering the inlet ports 75 and trifurcating into left and right primary airflows 103, and into a central secondary airflow 104, is minimized, while a high rate of concentration into the secondary airflow 104 of particles containing target material that were initially in the sampled airflow 102 is simultaneously realized.

The smoothly varying curvilinear profile of the rods 69 that form the sampled airflow inlet ports 75 contributes to a significant reduction in the pressure drop across the inlet ports 75 by minimizing expansion and contraction pressure drops in the sampled airflow 102. The distance between the sampled airflow inlet ports 75 and their respective secondary airflow inlet ports 76, and the shape and size of the curvilinear primary airflow channels 71 between the blades 47 and the inner surface 83 of the outer hub 80, are chosen so that sudden changes in the cross-section of the primary airflows 104 are minimized. This also means that all these characteristic features are of similar size, and that the entire air processor 12 is relatively shallow up to the secondary airflow inlet ports 76, reducing the volume and weight of the air processor 12.

It is known that particles containing target material that are about 5 microns or less in diameter tend to be very sticky, in the sense that if they impact on a physical surface they tend to adhere to, i.e., plate out on, that surface and are thus undesirably lost from whatever airflow that carries them.

However, it has been discovered that the curved, concave, sampled airflow inlet lobes 86 of each inlet pocket 84 help to minimize such losses of particles containing target material from the sampled airflow 102. This is because the curved nature of the sampled airflow inlet lobes 86 guide the incoming sampled airflow 102 so that it moves towards the rods 69 in curved flow paths which, as best seen in FIG. 6, rarely come into contact with the walls of the lobes 86 or with the outer surfaces of the rods 69. To ensure that a significant number of particles containing target material are not plated out on the surfaces of the lobes 86, it is necessary that the centrifugal forces associated with curved path airflow of the sampled airflow 102 adjacent to the surfaces of the lobes 86 be low. This may be done by using lobes 86 that have radii of curvature that are significantly larger than the radii of the rods 69. Since the velocities of the sampled airflow 102 are lower in the lobes 86, this also assists in minimizing plate-out of particles containing target material in the lobes 86.

In addition, it has also been discovered that since the rods 69 concentrate particles containing target material into the central portion of the sampled airflow 102 as it passes through the sampled airflow inlet slot 75 between the rods 69, the loss of particles containing target material from the sampled airflow 102 due to their stickiness is minimized since most of the particles containing target material are kept away from, and do not contact, the outer surfaces of the rods 69 as they flow through the sampled airflow inlet slot 75. In other words, the circumferential flow of the sampled airflow 102 immediately adjacent to the rods 69 creates a buffer layer of clean sample air (i.e., sample air from which most of the particles containing target material have been removed), between the rods 69 and the central portion of the sampled airflow 102 that passes between them.

In addition, most of the particles containing target material that are concentrated in the central portion of the sampled airflow 102 also do not contact the blade 47 as they pass through the blade 47's knife-edged secondary airflow inlet slot 76 and into the secondary airflow channel 73 within the blade 47.

Further, it has also been discovered that, due to the smooth, slowly varying symmetrical geometry of the secondary airflow channels 73 about an imaginary plane of symmetry that passes longitudinally through the center of the blade 47, loss of particles containing target material due to their sticking on the sides of the secondary airflow channels 73 may also be minimized.

All of the individual secondary airflows 104 in all of the blades 47, and all of the concentrated particles containing target material that they carry, flow radially inwardly through their respective secondary airflow channels 73, exit the blades 47 through their respective secondary airflow outlet slots 75, and enter the central cavity 95 of the inner hub 81 through their respective secondary airflow inlet slots 96 in the inner hub 81.

It is noted that all of the individual secondary airflows 104 are discharged radially inward into the central cavity 95 of the inner hub 81, towards the axis A, due to the radial arrangement of the blades 47 with respect to the inner hub 81.

It has been discovered that this radially inward discharge of the secondary airflows 104 desirably causes them to collide with each other in the central portion of the cavity 95, thereby effectively preventing any of the secondary airflows 104 from directly impacting the inner surface of the inner hub 81. It may be desirable to avoid a direct impact of any of the secondary airflows 104 on the inner surface of the inner hub 81 because if such a direct impact occurred, many of the particles containing target material in the impacting secondary airflow 104 may be undesirably lost by sticking to the inner surface of the inner hub 81.

The secondary airflow 104, and the concentrated particles containing target material that it carries, may then exit the inner hub 81 through the outlet fitting 77.

The inlet of any suitable air sampler, particle analyzer, or analytical device may be connected to the outlet fitting 77 in any suitable way. As has been mentioned, due to the "pressure recovery" effect that occurs in the secondary airflow channels 73, the air pressure of the secondary airflow 104 within the channels 73 may be closer to the ambient pressure of the sample air at the outer hub 80's sampled airflow inlet pockets 84 than would otherwise be the case. As a result, the air pressure of the secondary airflow 104 within the inner hub 81, and at the outlet fitting 77 may also be closer to the ambient pressure of the sample air at the outer hub 80's sampled airflow inlet pockets 84 than would otherwise be the case.

This "pressure recovery" effect may be useful because, for example, it may desirably reduce the amount of suction or negative pressure that the air sampler, particle analyzer, or analytical device may be required to provide to outlet fitting 77 in order to cause the secondary airflow 104, and the concentrated particles containing target material that it carries, to flow through the concentrator 10 and out through the outlet fitting 77, at any particular desired flow rate.

Several factors may be important in terms of designing the concentrator 10, such as the pressure-volume properties of the fan 16 that will be used to drive the concentrator 10. Other important factors may be certain relative dimensions, or ratios, of specific physical features of the concentrator 10, since the pressure drop and flow characteristics of the concentrator 10, as well as its ability to separate particles containing target material from the sampled airflow 102, may be dependent on these parameters.

Referring now to FIG. 6, the relative dimensions, or ratios, of importance may include the radius of a sampled airflow inlet lobe 86 relative to the radius of its respective rod 69; the radius of a rod 69 relative to the width of its respective sampled airflow inlet slot 75; the width of a sampled airflow inlet slot 75 relative to the distance to its respective secondary airflow inlet slot 76; and the rate at which the primary airflow channels 71 increase in width versus distance from the plane of symmetry.

For design purposes where the sampled airflow 102 is air, and where the particles containing target material have a density of about 1 g/cc and have a diameter in the range of from about 1 micron to about 10 microns, the following design relationships may provide some design guidance. The radius of a sampled airflow inlet lobe 86 may be on the order of about 5× to about 20× the radius of its respective rod 69; the radius of a rod 69 relative to its respective sampled airflow inlet slot 75 may be in the range of about 0.5 to about 2.0; the ratio of the width of a sampled airflow inlet slot 75 to the distance to its respective secondary airflow inlet slot 76 may be in the range from about 0.5 to about 2.0; the ratio of the width of the secondary airflow inlet slot 76 to the width of its respective sampled airflow inlet slot 74 may be in the range of from about 0.5 to about 1.5. Other dimensions may also assume importance, but the parameters herein noted may have the greatest effect on the flow rate of the sampled airflow 102 through the air processor 12 and the ability of the air processor 12 to concentrate particles containing target material in the secondary airflow 104.

It has been discovered that because of its novel construction, the concentrator 10 may offer many advantages over other devices. For example, it is unusually compact and light in weight for any given desired flow rate of the sampled airflow 102 through it. This may be due to such factors as: (a) the radial arrangement of its outer hub 80, blades 47 and inner hub 81 about its axis A; (b) the close spacing between its blades 47's sampled airflow inlet slots 75 and secondary airflow inlet slots 76; and (c) the relatively small amount of power that it consumes, resulting in a smaller, less powerful fan 16 being needed.

The concentrator 10's advantage of consuming relatively little power for any given desired flow rate of the sampled airflow 102 through it may be because the concentrator 10 requires a relatively small driving pressure difference between its sampled airflow inlet slots 75 and its primary airflow outlets 55. This relatively small driving pressure difference may be due to such factors as its curvilinear sampled airflow input structures (its rods 69) which transfer particles containing target material very efficiently, with only a small pressure drop, into the central portion of the sampled airflow 102 as it passes through the sampled airflow inlet slots 75. In addition, as best seen in FIG. 6, the primary airflow outlet slots 70 are sized with respect to the curvilinear primary airflow outlet channels 71 so that sudden changes in the flow cross sections of the sampled airflow 102 are minimized as it divides into left and right primary airflows 103, resulting in a small pressure drop between the slots 70 and the channels 71. Further, the close spacing between the sampled airflow inlet slots 75 and the secondary airflow inlet slots 76 results in a reduced pressure drop between the slots 75, 76. In addition, the radial arrangement of the concentrator 10's outer hub 80, blades 47 and inner hub 81 about its axis A results in relative short flow paths, and relatively small pressure drops, of the sampled, primary and secondary airflows 102, 103, 104 as they flow through the concentrator 10.

Example Concentrator 10

The various parts of the concentrator 10 are at least approximately shown to scale in the Figures. By way of example, the concentrator 10 may have an overall height of about 35.2 cm. Its fan plenum 15 may have a maximum diameter of about 23.8 cm and an overall height of about 17 cm.

The filter 44 for the outer hub 80 may be a coarse screen with openings about 0.6 cm square to prevent large debris from entering the outer hub 80. The outer hub 80 may have an outside diameter of about 16.7 cm and an inside diameter of about 14.8 cm. Each lobe 84 of a sampled airflow inlet pocket 84 in the outer hub 80 may be cylindrical in nature and have a circular cross section with a radius of about 0.65 cm. The sampled airflow inlet slots 90 in the inlet pockets 84 may be about 14 cm long and about 3.8 mm wide. Together, two lobes 84 and their respective inlet slot 90 create an opening in the outer surface 82 of outer hub 80 that is 2.29 cm wide.

Each blade 47 may be about 6.1 mm thick, as measured between the outer surfaces of its two blade elements 60. The outer edges 72 of the blade bodies 61 of each blade 47 may be tapered at an angle of about 75° with respect to an imaginary plane of symmetry that passes longitudinally through the center of the blade 47. The rods 69 of a blade 47 may be about 1.6 mm in diameter and each sampled airflow inlet slot 75 between the rods 69 may be about 0.61 mm wide and about 6.7 cm long.

Each secondary airflow channel 73 in a blade 47 may have a knife-edge secondary airflow inlet slot 76 having a width of about 0.61 mm, which may match the 0.61 mm width of its corresponding sampled airflow inlet slot 75. The inlet slot 76 may be about 0.5 mm downstream from the lowest point of the rods 69, as best shown in FIG. 6. This distance may usefully fall within the range of about 0.3 mm to about 0.8 mm.

Each secondary airflow channel 73 may have a length of about 4.75 cm, as measured between its secondary airflow inlet and outlet slots 75, 105.

Figure 5A:
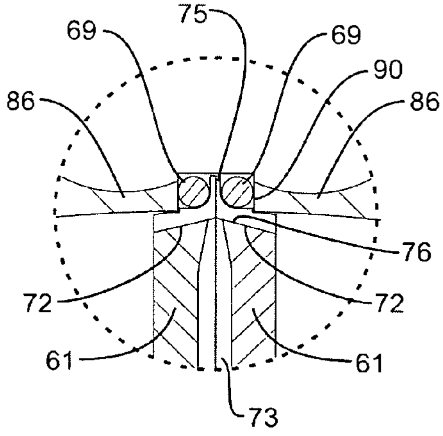
FIG. 5A is an enlarged view of the circled portion 5A in FIG. 5.
Figure 5B:
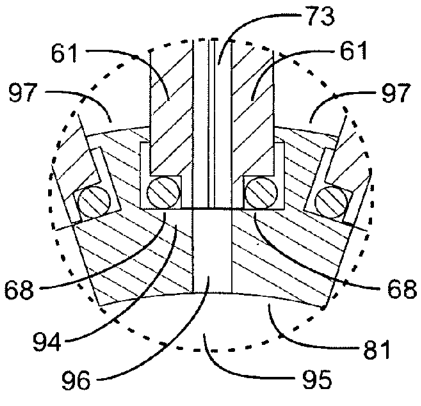
FIG. 5B is an enlarged view of the circled portion 5B in FIG. 5.
Figure 15:
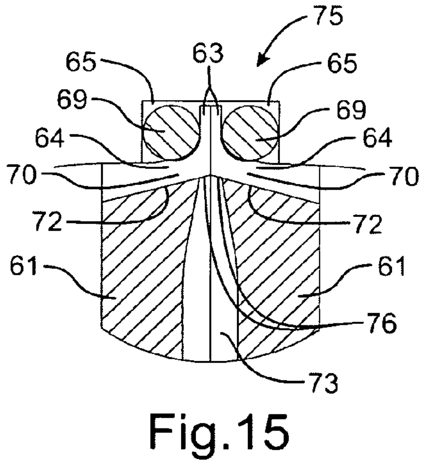
FIG. 15 is an enlarged view of the circled portion 15 in FIG. 14.
Figure 16:
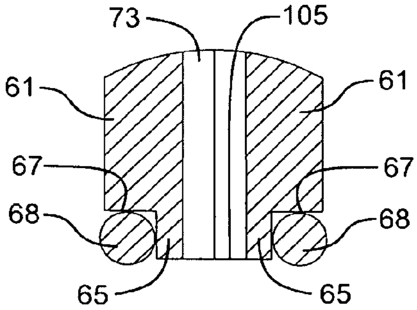
FIG. 16 is an enlarged view of the circled portion 16 in FIG. 14.

The width of each secondary airflow channel 73 may increase from its 0.61 width at its inlet slot 76 to a width of about 0.15 cm over a distance of about 0.25 cm downstream from its inlet slot 76, as best seen in FIGS. 5A, 6 and 15. This increase in the width of the secondary airflow channel 73 may be due to its sidewalls within the blade bodies 61 diverging at about a 10 degree angle with respect to an imaginary plane of symmetry that passes longitudinally through the center of the blade 47, before its sidewalls become parallel to each other about 0.25 cm downstream from the inlet slot 76.

The inner hub 81 may have an internal diameter of about 4.3 cm, with the internal diameter of the outlet fitting 77 being somewhat less.

Test Results for Example Concentrator 10

For the tests, the fan assembly 11 for the example concentrator 10 was selected to enable the concentrator 10 to have a flow rate of the sampled airflow 102 through it in the range of about 3,000 to 3,600 LPM. When the example concentrator 10 was operated at these flow rates, its total electric power consumption rate was measured to be only 50 to 90 watts.

Figure 20:
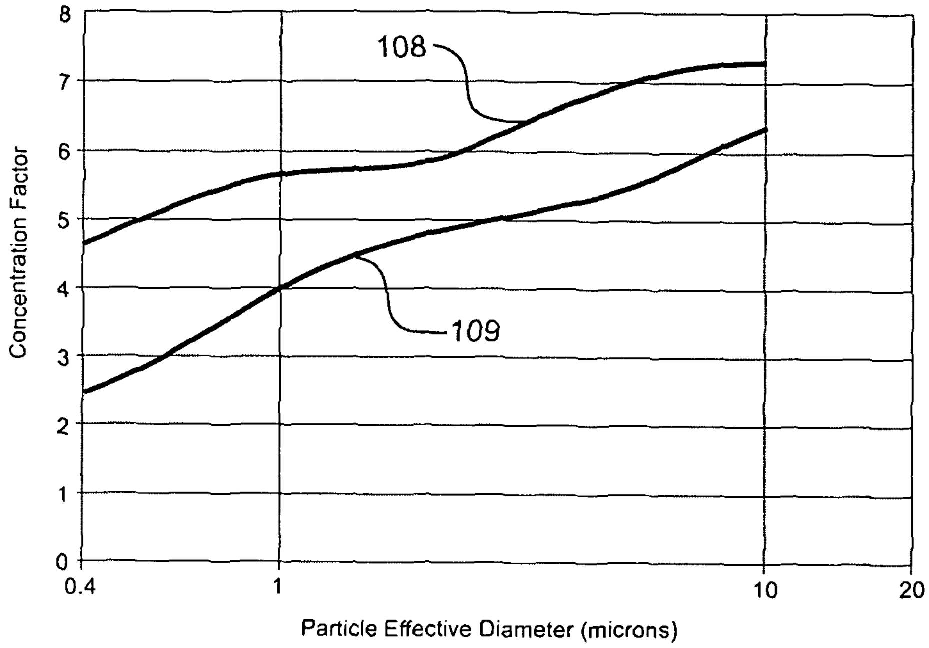
FIGS. 20-21 are graphs showing certain performance characteristics of the concentrator 10.

The curves 108, 109 in FIG. 20 show typical data for the Concentration Factor as a function of the Particle Effective Diameter. The Particle Effective Diameter is the effective diameter of the test particles in the sampled airflow 102. To generate the curves 108, 109, the flow rate of the sampled airflow 102 was 3,600 LPM and 3,000 LPM, respectively; while the flow rate of the secondary airflow 104 was held constant at 300 LPM.

The Concentration Factor was determined by taking the ratio of the number of test particles per unit volume in the secondary airflow 104 and the number of test particles per unit volume in the incoming sampled airflow 102. For example, if the secondary airflow 104 had ten test particles per unit volume, and the sampled airflow 102 had two test particles per unit volume, then the Concentration Factor would be five (i.e., 10/2=5).

The test particles that were used in the tests were made by the Duke Scientific Corporation of Palo Alto, Calif. and were fluorescent polystyrene micro spheres, and fragments thereof, having a density of 1.05 g/cc. The curves 108, 109 were determined from multiple test runs using a Met One 200 L laser particle counter, made by Met One Instruments, Inc. of Grants Pass, Oreg., to count the number of test particles per unit volume in the sampled airflow 102 and in the secondary airflow 104.

The curves 108, 109 show that the test particles of 1.05 g/cc (which is typical of particles of organic target material), and that had effective optical diameters in the range of 0.5 to 1.0 microns were concentrated by a factor of 3× to 5.6×. Test particles in the range of 1.0 to 2.0 microns were concentrated by a factor of 4× to 5.8×, while 10-micron test particles were concentrated by a factor of about 6.4× to 7.3×.

Figure 21:
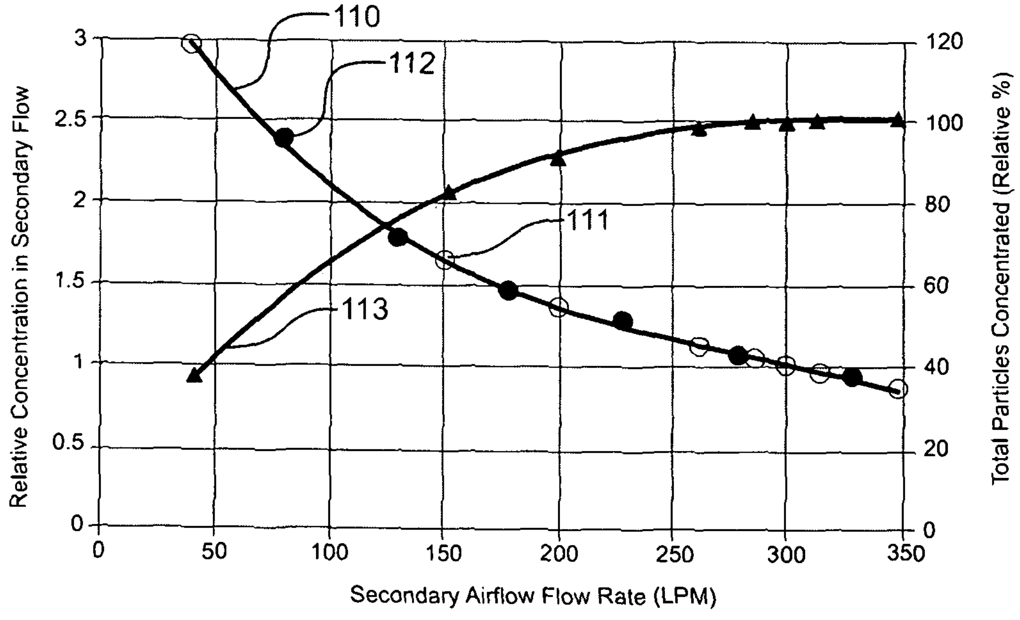

Referring now to FIG. 21, its curve 110 shows the Relative Concentration in Secondary Airflow as a function of the Secondary Airflow Flow Rate. The Relative Concentration in Secondary Airflow is the relative concentration of the test particles in the secondary airflow 104, as compared to the Concentration Factor in FIG. 20. The Secondary Airflow Flow Rate is the flow rate of the secondary airflow 104. The open circle data points 111 on the curve 110 are theoretical data points, while the solid circle data points 112 on the curve 110 are actual data points.

As shown by the curve 110, reducing the flow rate of the secondary airflow 104 can significantly further enhance the concentration of the test particles in the secondary airflow 104. For example, at a flow rate of the secondary airflow 104 of about 40 LPM, the curve 110 shows that the Concentration Factors shown in FIG. 20 are increased by about 3×. In other words, for 1.0-micron test particles the Concentration Factors of 4.0× to 5.6× shown in FIG. 20 are increased to about 12× to 16.8×; for 2.0-micron test particles the Concentration Factors of 4.6× to 5.8× shown in FIG. 20 are increased to about 13.8× to 17.4×; and for 10.0-micron test particles the Concentration Factors of 6.4× to 7.3× shown in FIG. 20 are increased to about 19.2× to 21.9×.

Curve 113 in FIG. 21 shows the Total Particles Concentrated (Relative %) as a function of the Secondary Airflow Flow Rate of the secondary airflow 104. The Total Particles Concentrated (Relative %) is the relative percentage of test particles in the sampled airflow 102 that appeared in the concentrator 10's secondary airflow 104, normalized to collection performance at a flow rate of the secondary airflow 104 of 300 LPM (300 LPM=100%).

Curve 113 shows that the percentage of test particles that are concentrated in the secondary airflow 104 begins to fall for flow rates of the secondary airflow 104 that are below about 250 LPM, which is about 8% of the flow rate of a sampled airflow 102 having a flow rate of 3,000 LPM, and which is about 7% of the flow rate of a sampled airflow 102 having a flow rate of 3,600 LPM. It is theorized that the collection efficiency eventually falls as the flow rate of the secondary airflow 104 decreases because a certain flow rate of the secondary airflow 104 is required to fully deplete the central portion of the sampled airflow 102 immediately in front of the secondary airflow inlet slot 76 into which the test particles were concentrated.

Concentrator 10*a*

Turning now to FIGS. 17-19, the concentrator 10*a* is the same as, or at least similar to, the concentrator 10 of FIGS. 1-16 in all respects, except for those differences which will be made apparent by all of the disclosures herein. In addition, for clarity and simplicity, certain parts of the concentrator 10*a* of FIGS. 17-19 have been given the same reference numerals, with an "a" suffix, as the reference numerals used for the corresponding respective parts of the concentrator 10 of FIGS. 1-16.

In general, the primary conceptual difference between the concentrator 10 and the concentrator 10*a* may be that the concentrator 10*a* has been modified so that it may serve the additional function of being its own air sampler, particle analyzer or analytical device, i.e., so that it may remove the particles containing target material from the secondary airflow 104, so that the removed particles containing target material may be observed, examined, tested and evaluated.

As seen in FIGS. 17-19, the lower portion of the concentrator 10*a*'s air processor 12 may have a filter assembly comprising a bottom end plate 43*a*; a seal 116; a filter 117 that may have a filter element 118; a filter holder 119; a filter support 120; a filter adapter 121; and mounting feet 49*a* that may also be used to releasably assemble the filter adapter 121 to the bottom of the bottom plate 43*a*.

The bottom plate 43*a* may have four secondary airflow outlet ports 122, a support ring 123 for the inner hub 81, and four arms 124 for supporting the support ring 123. The bottom of the support ring 123 may have an annular groove 134 for the seal 116. The bottom plate 43*a* may also have an annular groove 57*a* for receiving the bottom edge of the filter 44, an annular recess 58*a* for receiving the bottom end 88 of the outer hub 80, and an opening 59*a* in the support ring 123 for receiving the bottom neck 99 and O-ring 101 of the inner hub 81.

The filter element 118 may comprise any suitable filter media and may be selected to be able to remove from the secondary airflow 104 the particular kind of particles containing target material that may be of interest to the user of the concentrator 10*a*. The filter holder 119 may be of any suitable construction and may have for example, a filter holder handle 124 and a filter holder ring 125 to which the filter element 118 may be assembled. Alternatively, the filter holder 119 may be eliminated, in which case the filter element 118 may be held in place by the filter support 120.

The filter support 120 may have a support ring 126 and four support legs 127. The filter adapter 121 may have a rim 128, three mounting notches 129 and a filter cup 130. Each mounting foot 49*a* may have a filter adapter notch 131 and a bore 132 into which a spring loaded pin assembly 133 has been assembled.

The forgoing components of the concentrator 10*a* may be assembled in any suitable way, such as by assembling the seal 116 in its groove 133 in the bottom of the inner hub support ring 123. The filter element 118 may be assembled to the filter holder ring 125 or the filter element 118 may have been pre-assembled to the filter holder ring 125.

The filter support 120 may be assembled to the adapter 121 by assembling its support legs 127 to any suitable locations on the inside of the bottom of the adapter 121's filter cup 130, and the mounting feet 49*a* may be assembled to any suitable locations on the outside of the bottom of the adapter 121's filter cup 130. The filter 117 may be releasably assembled to the filter support 120 by placing the filter holder ring 125 onto the support ring 126.

The adapter 121 may then be releasably assembled to the bottom of the bottom plate 43*a* by locating the mounting feet 49*a* in the notches 129 in its rim 128, as best seen in FIG. 19, and by then moving the adapter 121 towards the bottom plate 43*a* until its rim 128 touches the bottom of the bottom plate 43*a*. The adapter 121 may then be rotated until the edges of its rim 128 that are adjacent to its notches 129 enter respective notches 131 in the mounting feet 49*a*, and are releasably held in place there by the spring loaded pins 133 in the mounting feet 49*a*. When the adapter 121 and the bottom plate 43*a* are assembled together, there may be a fluid-tight seal between: (a) the support ring 126, the filter holder ring 125, the seal 116 and the bottom of the bottom plate 43*a*; and (b) between the adapter 121's rim 128 and the bottom of the bottom plate 43*a*.

To remove or replace the filter 117 after it has been used, the adapter 121 may be rotated until the edges of its rim 128 that are adjacent to its notches 129 leave their respective notches 131 in the mounting feet 49*a*, and are no longer engaged by the spring loaded pins 133, at which time the adapter 121 may then be removed from the bottom of the bottom plate 43*a*.

In the example concentrator 10 which was described above, when the sampled airflow 102 had a flow rate of about 3,600 LPM, and the secondary airflow 104 had a flow rate of about 300 LPM, the static pressure of the primary airflow 103 within the central cavity 97 of the outer hub 80 may be about −4.6 cm of water, relative to the ambient pressure of the sampled airflow 102 that surrounds the outer hub 80. On the other hand, the static pressure of the secondary airflow 104 within the central cavity 95 of the inner hub 81 may be about −0.25 to about −0.4 cm of water relative to the ambient pressure of the sampled airflow 102 that surrounds the outer hub 80. Therefore there is a static pressure differential of at least about 4.2 cm of water between the relatively higher pressure secondary airflow 104 in the central cavity 95 of the inner hub 81, and the relatively lower pressure primary airflow 103 in the central cavity 97 of the outer hub 80.

The concentrator 10*a* uses this static pressure differential so that the relatively higher pressure secondary airflow 104 in the central cavity 95 of the inner hub 81 will sequentially flow: (a) through the filter element 118 (which will remove the particles containing target material from the secondary airflow 104 passing through it), (b) into the cavity 135 in the adapter 121's cup 130, (c) out of the cavity 135 through the secondary airflow outlet ports 122 in the bottom plate 43*a*, (d) into the central cavity 97 of the outer hub 81 between the blades 47 (where the secondary airflow 104 will mix with the primary airflow 103), (e) out of the cavity 97 through the air outlets 55 in the top plate 42, and (f) and out through the fan assembly 11 in the manner previously described for the primary airflow 103 of the concentrator 10.

This means that the concentrator 10*a* may serve the dual functions of: (a) concentrating the particles containing target material from a high flow rate sampled airflow 102 into a low flow rate secondary airflow 104, and (b) serving as an air sampler, particle analyzer or analytical device by removing the particles containing target material from the low flow rate secondary airflow 104 in any suitable way, such as by using the filter 117.

Thus, the concentrator 10*a* offers many advantages. For example, it eliminates the need for a separate air sampler, particle analyzer or analytical device to remove the particles containing target material from the secondary airflow 104; and its low flow rate secondary airflow 104 through its filter 117 will help to prevent damage to particles containing target material that are delicate, such as if the particles containing target material were organisms. In addition, because of the low flow rate of the secondary airflow 104, the surface area of the filter element 118 in its filter 117 may be selected to minimize the volume or area of the filter element 118, thereby potentially maximizing the efficiency with which the particles containing target material that the filter element 118 removed from the secondary airflow 104 can be extracted from the filter element 118, as compared to a filter element 118 that was sized in area or volume to remove particles containing target material from a high flow rate sampled airflow 102.

Some alternative constructions of the concentrator 10*a* will now be described. First, the filter support 120 may be eliminated, in which case the filter 117 may be releasably assembled directly to the bottom of the hub support ring 123 over the opening 59*a* in any suitable way.

Second, the filter 117 and filter support 120 may both be eliminated, and the circular filter 117 may be replaced by one or more annular filter segments 117 that may be releasably secured in any suitable way to the bottom of the bottom plate 43*a* over the secondary airflow outlet ports 122.

Third, the adapter 121 may be releasably assembled to the bottom of the bottom plate 43*a* in any suitable way other than that which was described above; and the adapter 121 may have any other suitable size, shape and construction as long as it is operable to convey the secondary airflow 104 from the opening 59*a* to the secondary airflow outlet ports 122.

Example Uses of the Concentrators 10, 10*a*, 10*b*

Contraband is a serious problem at ports worldwide, and devices are needed that will efficiently interrogate shipping containers 137 (see FIG. 23) of various sizes, ranging from aircraft shipping containers to 40-foot ocean-going shipping containers. By interrogation, it is meant that particles containing target material in the sample air within the shipping containers 137 are removed from such sample air, such as for observation, identification, examination, testing or analysis. The particles containing target material may be particles of any material of interest, such as particles of drugs, explosives, and biowarfare materials.

The concentrators 10, 10*a*, and 10*b* may be particularly helpful in any situation where large volumes of sampled airflow 102 must be processed during the interrogation of the shipping container 137, and it is desired that the processing time be minimized, whether the large volumes of sampled airflow 102 are from shipping containers 137, or from any other wholly or partially enclosed spaces of interest, such as sports auditoriums and conference halls. In general, any such wholly or partially enclosed space of interest may be called a "sample space".

After the concentrators 10, 10*b* have processed the sampled airflow 102, particles containing target material may be removed from their respective secondary airflows 104 by any suitable air sampler, particle analyzer, or analytical device that may be connected to their respective outlet fittings 77. On the other hand, it may not be advantageous to connect a separate air sampler, particle analyzer, or analytical device to the concentrator 10*a*, since its filter element 118 will remove particles containing target material from its secondary airflow 104.

By way of example, the use of the concentrator 10*b* to interrogate an ocean going shipping container 137 will now be described, it being understood that the same or similar comments will apply to using any of the concentrators 10, 10*a*, 10*b* to interrogate any other wholly or partially enclosed space.

An ocean-going shipping container 137 may have an interior volume of up to 50,000 liters, or more. The concentrator 10*b* may have the same performance characteristics that were described above regarding the example concentrator 10, i.e. the concentrator 10*b* may produce and process a sampled airflow 102 having a flow rate of about 3,600 LPM. Thus, even if the container 137 were entirely empty of contents 144, the concentrator 10*b* would be able to process one turn of air from inside such a container 137 in only about fourteen minutes. By comparison, typical portable air samplers, particle analyzers, and analytical devices may process a sampled airflow 102 in the range of about 150 to 500 LPM. Accordingly, such devices would take from about 1.7 to about 5.6 hours to process one turn of air from inside such a container 137, which may be an unacceptably long period of time in view of the large number of containers 137 that may need to be interrogated, and the speed with which dockside transfer procedures for containers 137 are carried out.

From the above it is seen that the concentrator 10*b* may be able to process the air from such a container 137 from 7× to 24× faster than a typical portable air sampler, particle analyzer or analytical device.

In addition, like the concentrator 10, the concentrator 10*b* may be easily designed (e.g., by being scaled up in size), so as to be able to produce and process a sampled airflow 102 having any desired flow rate, thereby reducing even further the amount of time it would take for the concentrator 10*b* to process one turn of air from inside a shipping container 137.

The concentrator 10*b* may be used to interrogate a shipping container 137 in any number of ways. For example, it (and its associated air sampler, particle analyzer, or analytical device that is connected to its outlet fitting 77) may be placed within the container 137. The concentrator 10*b* may have several useful attributes for efficient interrogation when it is placed within the container 137. First, it is compact. Second, it collects sampled air from within the container 137 over a 360° radial swath, providing effective sampling of the largest lateral area possible.

Third, the discharge of the primary airflow 103 from its fan plenum 15 in the form of a jet of air may offer the advantages of: (a) being very effective at sweeping the container 137's inner surfaces and the outer surfaces of its contents 144, to release into the air within the container 137 particles containing target material from the container 137's interior surfaces and from the outer surfaces of its contents 144; and (b) producing an induced draft effect that may desirably cause the circular sensing radius of the concentrator 10*b* to more than double by causing a desirable inward flow of the air within the container towards the concentrator 10*b*'s inlet 149. In other words, the induced draft effect may create large circulating air patterns within the container 137 that ensure more effective sampling of the entire internal volume of the container 137, since the circulating patterns may serve to move air from even the most remote portions of the container 137 towards the concentrator 10*b*.

Alternatively, any other suitable air-moving device other than the concentrator 10*b* may provide the jet of air.

As seen in FIG. 23, another way to use the concentrator 10*b* to interrogate a shipping container 137 may be to locate the concentrator 10*b* (and its associated air sampler, particle analyzer, or analytical device that is connected to its outlet fitting 77), outside of the container 137.

In this event, the container 137 may be provided with any suitable inlet and outlet ports 138, 139 having any suitable size, shape and construction. The ports 138, 139 may located in any suitable location in any of the container's sidewalls 161, doors 162, top 163, or bottom 164 in order to access the airspace 143 within the container 137. Preferably, the ports 138, 139 may be located near the top of the container 137's sidewalls 161 in order to access the air space 143 that is typically found within the container 137 over the contents 144, even when the container 137 is considered to be fully loaded.

Placing the ports 138, 139 in the doors 162 may be more practical than other alternatives because it may be, for example, easier and less expensive to retrofit ports 138, 139 into the doors 162, or to replace doors 162 without ports 138, 139 with doors 162 having ports 138, 139, than it would be to create the necessary ports 138, 139 in the container 137's sidewalls 161, top 163 or bottom 164.

The inlet 149 of the concentrator 10*b*'s shroud 147 may be fluidly connected to the container 137's outlet port 139 in any suitable way, such as by using any suitable input duct 141 of any suitable size, shape and construction. The duct 141 may convey the sampled airflow 102 from the interior of the container 137 to the shroud 147 of the concentrator 10*b*.

An optional output duct 142 may fluidly connect the outlet 23 of the fan plenum 15 to the container 137's inlet port 138. Any suitable duct 142 may be used, which may be of any suitable size, shape and construction. If a duct 142 is used, it may convey the primary airflow 103 from the fan plenum 15 to the container 137's inlet port 138.

During operation of the concentrator 10*b* of FIG. 23, its fan assembly 11 will create a negative air pressure at the primarily airflow outlets 55 of the air processor 12 that will enable the relatively higher pressure sampled air in the container 137 to form a sampled airflow 102 that will flow from, the airspace 143 in the container 137, through the input duct 141 to the annular airspace inside of the shroud 147, and then through the air processor 12. The primary airflow 103 from its fan assembly 11 may then flow through the output duct 142 to the container 137's inlet port 138, where it may re-enter the airspace 143 in the container 137. The secondary airflow 104 (and the particles containing target material that it carries), may exit the concentrator 10*b* through the outlet fitting 77, to which any suitable low flow rate air sampler, particle analyzer, or analytical device may be connected.

It has been discovered that a desirable circulatory airflow pattern 145 within the container 137's airspace 143 may be created if the ports 138, 139 are, as seen in FIG. 23, located in the same sidewall 161 of the container 137, are located near the top of that sidewall 161, and are located near the corners formed by their respective adjacent sidewalls 161. In FIG. 23, the sidewall 161 in which the ports 138, 139 are located comprises the container 137's doors 162. Alternatively, either or both of the ports 138, 139 may be located in the container 137's top or bottom 163, 164.

By so locating the ports 138, 139 as seen in FIG. 23, the returning primary airflow 103 from the concentrator 10*b*'s output duct 142 will enter the airspace 143 within the container 137 through its inlet port 138 as a jet of high velocity, axially-directed air, which creates a desirable circulatory airflow pattern 145 in the airspace 143. Corner injection of the primary airflow 103 through the container 137's inlet port 138 into the airspace 143 in the form of a jet of air ensures good penetration of the primary airflow 103 into the container 137 and helps ensure that even sample air in the remotest parts of the container 137 may exit the container 137 through its outlet port 139 and enter the concentrator 10*b* through its input duct 141.

As an added benefit, circulating the primary airflow 103 in this manner back into the container 137 minimizes exposure of dock personnel to any dangerous particles containing target material (or any other dangerous particles) that may be present in the primary airflow 103. However, as an alternative, the duct 142 may be eliminated so that the primary airflow 103 may be ejected into the air in the vicinity of the concentrator 10*b*, rather than back into the container 137.

Vibrating the Container 137 and its Contents 144

During use and shipment of the container 137, it is highly likely that a significant number of particles containing target material may have been released into the air within the container 137 by its contents 144. Many of such particles containing target material may have then adhered themselves to the internal surfaces of the container 137 and to the external surfaces of the contents 144.

It has been discovered that if the walls of the container 137 are vibrated (which will then also vibrate the contents 144), such vibrations of the walls of the container 137 and contents 144 may desirably cause at least some of these adhering particles containing target material to be desirably released into the air within the container 137 from the internal surfaces of the container 137 and from the external surfaces of the contents 144. This may be done either before, or during, the use of the concentrators 10, 10*a*, 10*b* to process the air within the container 137.

In the following discussion, vibrating just the container 137 will be discussed, it being understood that vibrating the container 137 will always cause the contents 144 within the container to also vibrate.

Any suitable vibration apparatus may be used to vibrate the container 137, in any suitable way. One or more of the vibration apparatus may be removably or permanently assembled to the container 137 in any suitable way, such as by using mechanical or magnetic fasteners; interference fits; friction fits; barbed, threaded, bonded, glued or welded connections; splines; keys; or mechanical couplers.

Figure 24:
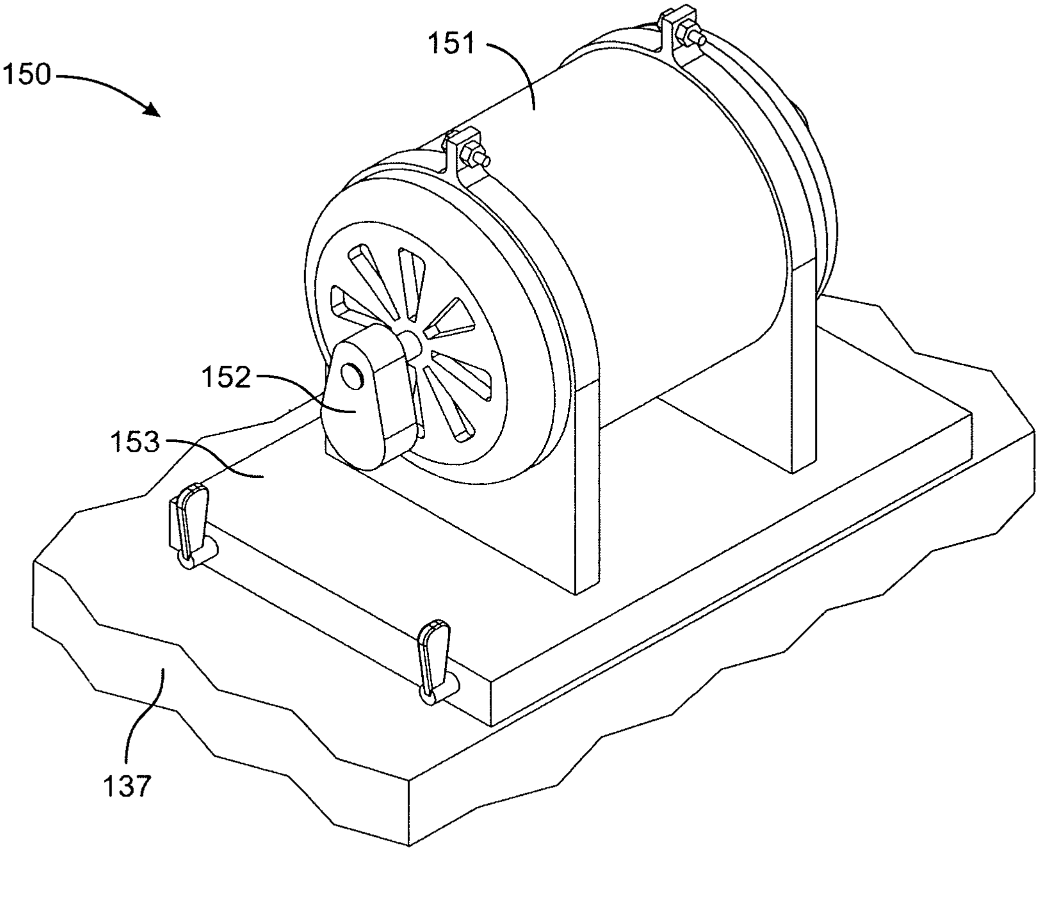
FIG. 24 is a perspective view of a mechanical vibrator 150, taken from an upper aspect.

For example, the vibration apparatus may be any suitable electric, pneumatic, or hydraulic mechanical vibrator having any suitable size, shape and construction, such as the mechanical vibrator 150 that is illustrated in FIG. 24. The vibrator 150 may comprise any suitable motor 151 assembled to a base 153 that may be assembled to the container 137. The motor 151 may rotate an eccentric weight 152. As the eccentric weight 152 rotates, it subjects the container 137 to a strong vibration. There is nothing per se novel about the vibrator 150, except for its size, since this manner of generating vibrations is commonly used (on a much smaller scale) for ringless cell phone annunciators.

As a further example, if the container 137 is made from steel, the vibration apparatus may comprise any suitable electromagnetic vibrator of any suitable size, shape and construction that may be used to electromagnetically vibrate the container 137 in any suitable way. This will, in essence, turn the part of the container 137 that is located beneath the electromagnetic vibrator into a sort of loudspeaker. This is because during operation of the electromagnetic vibrator, the part of the container 137 that is located beneath it will form a magnetically permeable diaphragm, which may be made to move in and out in response to the magnetic forces applied to it by a closely coupled electromagnet that forms part of the electromagnetic vibrator.

Figure 25:
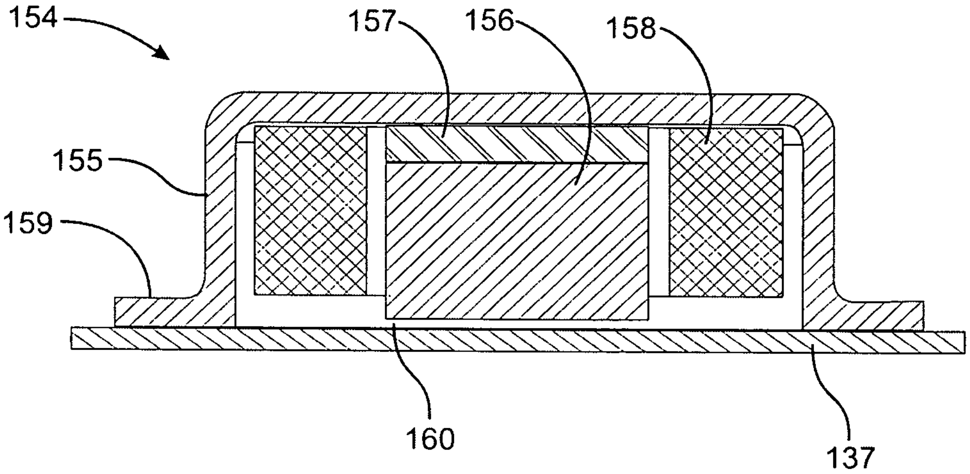
FIG. 25 is a cross-sectional view of an electromagnetic vibrator.

An example of an electromagnetic vibrator 154 is illustrated in FIG. 25, and may comprise a cylindrical magnetically permeable housing 155 having a circular cross-sectional profile, a cylindrical magnetically permeable core piece 156, a cylindrical optional permanent magnet 157, and an annular electromagnetic winding 158 that encircles the core piece 156. Together, the core piece 156 and the winding 158 form a powerful electromagnet.

The magnet 157 and winding 158 may be assembled to the interior of the housing 155, and the core piece 156 may be assembled to the magnet 157. Alternatively, if there is no magnet 157, then the core piece 156 may be assembled to the interior of the housing 155. The housing 155's annular rim 159 may be releasably or permanently assembled to the container 137, with a small air gap 160 being located between the container 137 and the core piece 156.

If the vibrator 154 includes a permanent magnet 157, the functions of the magnet 157 may include biasing the vibrator 154's magnetic operating point in any desirably way, or assisting in magnetically assembling the vibrator 154 to the container 137.

During operation of the vibrator 154, when a sinusoidal drive current is applied to its electromagnetic winding 158, the magnetic force across the air gap 160 will vary as a function of the applied sinusoidal drive current, causing the part of the magnetically permeable container 137 that is located beneath the vibrator 154 to vibrate in and out, thereby turning that part of the container 137 into a loudspeaker element.

As an alternative, the housing 155 may have any suitable geometric or non-geometric cross-sectional profile other than circular. For example the housing 155 may have a square or rectangular cross-sectional profile, and be sized so as to fit between the reinforcing ribs that often form part of the sidewalls of a container 137.

As a further alternative, the vibration apparatus may comprise any suitable magnetostrictive or piezoelectric solenoid, which may replace the electromagnetic vibrator 154. In such an event the part of the container 137 that is located beneath the solenoid may serve as an acoustic transducer that vibrates in and out as a function of the forces applied to it by the solenoid.

As another alternative, the vibration apparatus may comprise any suitable acoustic transducer of any suitable size, shape and construction, which may be assembled to the exterior of the container 137 in any suitable way, or which may be located within the container 137 in any suitable way. In either event, the acoustic transducer may be used to cause the container 137 to vibrate in any suitable way.

As a further alternative, the vibration apparatus may comprise acoustic energy itself, in which case the acoustic energy may be introduced into the interior of the container 137 in any suitable way, such as through any suitable opening in the container 137, such through its inlet or outlet ports 138, 139, in order to vibrate the container 137.

It is known that if acoustic energy is injected into one end of a closed-ended structure, at certain frequencies one or more acoustic resonances, i.e., standing waves, will form within the structure. It has been discovered that such acoustic resonances may be used to more effectively vibrate the container 137 as compared to if no acoustic resonances were formed within the container 137 by the inputted acoustic energy.

Although forming a single fundamental acoustic resonance within the container 137 may have some value, it has been further discovered that injecting a range of frequencies of acoustic energy into the container 137 may vibrate the container 137 even more effectively, because the antinodes of the acoustic energy resonances will travel down the length of the container 137 and provide, in effect, desirable acoustic energy resonance peaks at different points along the length of the container 137. At resonance, the acoustic level in the container 137 may be considerable higher than at the input source, since each cycle of the inputted acoustic energy serves to constructively build upon the previous cycle.

It is well known that odd-harmonics are resonant, so that the first harmonic for the container 137 would have a wavelength of four times the length of the container 137, the third harmonic would have a wavelength of four-thirds of the length of the container 137, and so on. For example, for a typical 40-foot shipping container 137, the fundamental resonant frequency in air at 25° C. is about 7.1 hz. Any suitable mechanical vibrator 150, electromagnetic vibrator 154, magnetorestrictive solenoid, piezoelectric solenoid, or acoustic transducer, such as a conventional loudspeaker may easily generate this fundamental resonant frequency, and the first few odd harmonics, in any suitable way.

It has been discovered that cycling the acoustic energy within the container 137 between odd harmonic resonances will cause the container 137 to strongly vibrate.

Either or both of the container 137's ports 138, 139 may also be used to inject acoustic energy into the container 137 at frequencies that are selected to generate resonant acoustic energy peaks that travel longitudinally back and forth within the container 137, to vibrate the container 137.

More complex or more robust acoustic energy patterns or resonances may be generated within the container 137 if acoustic energy is introduced into the container 137 through both of its ports 138, 139 simultaneously, or by varying the phase and frequency of the longitudinal acoustic energy patterns or resonances that are created within the container 137.

As another alternative, the container 137 may be caused to vibrate by placing it on any suitable shaker device of any suitable size, shape and construction.

It is to be understood that, without departing from the scope and spirit of the claimed invention, any particular part of any of the concentrators 10, 10*a*, 10*b* may be suitably combined or formed with one or more of the other parts of its respective concentrator 10, 10*a*, 10*b* to form one integral or composite part; that any particular part of any of the concentrators 10, 10*a*, 10*b* that may be made in one piece may instead be made by assembling together in any suitable way, two or more sub-pieces; and that the various parts of each of the concentrators 10, 10*a*, 10*b* may be assembled together in any suitable ways other than those described herein, such by using fasteners; interference fits, friction fits; barbed, threaded, bonded, glued or welded connections; splines; keys; or mechanical couplers.

It is also to be understood that the specific embodiments of the claimed invention that are disclosed herein were disclosed strictly by way of non-limiting example. Accordingly, various modifications may be made to those embodiments without deviating from the scope and spirit of the claimed invention. Additionally, certain aspects of the claimed invention that were described in the context of a particular embodiment may be combined or eliminated in other embodiments. Although advantages associated with a certain embodiment of the claimed invention have been described in the context of that embodiment, other of the embodiments may also exhibit such advantages. Further, not all embodiments need necessarily exhibit any or all of such advantages in order to fall within the scope of the claimed invention.

When the phrase "at least one of" is used in any of the claims, that phrase is defined to mean that any one, any more than one, or all, of the listed things or steps following that phrase is, or are, part of the claimed invention. For example, if a hypothetical claim recited "at least one of A, B, and C", then the claim is to be interpreted so that it may comprise (in addition to anything else recited in the claim), an A alone, a B alone, a C alone, both A and B, both A and C, both B and C, and/or all of A, B and C.

Before an element in a claim is construed as claiming a means for performing a specified function under 35 USC section 112, last paragraph, the words "means for" must be used in conjunction with that element.

As used herein, except in the claims, the words "and" and "or" are each defined to also carry the meaning of "and/or".

In view of all of the disclosures herein, these and further modifications, adaptations and variations of the claimed invention will now be apparent to those of ordinary skill in the art to which it pertains, within the scope of the following claims.

What is claimed is:

1. A concentrator, wherein said concentrator comprises an air processor that comprises:

a sampled airflow inlet slot that is operable to receive a sampled airflow that contains particles containing target material; and a secondary airflow inlet slot that is located downstream from said sampled airflow inlet slot;

wherein said sampled airflow inlet slot is operable to use centrifugal force to concentrate at least some of said particles containing target material into a central portion of said sampled airflow as said sampled airflow flows through said sampled airflow inlet slot;

wherein said sampled airflow inlet slot is operable to produce a non-collimated sampled airflow as said sampled airflow flows through said sampled airflow inlet slot;

wherein said sampled airflow inlet slot and said secondary airflow inlet slot share a common plane of symmetry;

wherein said secondary airflow inlet slot is operable to divide a secondary airflow from at least a part of said central portion of said sampled airflow that is received by said secondary airflow inlet slot from said sampled airflow inlet slot, is operable to divide a left primary airflow from at least a part of a left portion of said sampled airflow that is received by said secondary airflow inlet slot from said sampled airflow inlet slot, and is operable to divide a right primary airflow from at least a part of a right portion of said sampled airflow that is received by said secondary airflow inlet slot from said sampled airflow inlet slot; and wherein said secondary airflow flows through said secondary airflow inlet slot.

2. The concentrator of claim 1, wherein said air processor further comprises a sampled airflow inlet pocket comprising concave left and right sampled airflow inlet lobes through which at least part of said sampled airflow flows before entering said sampled airflow inlet slot; and wherein each of said sampled airflow inlet lobes has a curved profile and is operable to impart a rotary motion to a respective part of said sampled airflow.

3. The concentrator of claim 1, wherein said air processor further comprises a pair of rods; wherein each said rod has a respective outer surface; wherein at least a portion of each said respective outer surface is convex; and wherein said sampled airflow inlet slot is formed by said convex outer surfaces of said pair of rods.

4. The concentrator of claim 1, wherein said left and right primary airflows have a combined flow rate; wherein said secondary air flow has a flow rate; and wherein said flow rate of said secondary air flow is less than about 1% of said combined flow rate of said primary airflows.

5. The concentrator of claim 1, wherein said air processor further comprises a central longitudinal axis and at least two blades; wherein each said blade comprises a respective said sampled airflow inlet slot; a respective said secondary airflow inlet slot, and a respective blade secondary airflow outlet port; wherein a respective said secondary airflow exits from each said blade secondary airflow outlet port; wherein said blades are radially arranged about said axis; and wherein said respective said secondary airflows flow radially inwardly toward each other and toward said axis.

6. The concentrator of claim 1, wherein said sampled airflow inlet slot has a pair of sides; wherein each of said sides has a respective upstream surface at a point where said sampled airflow enters said sampled airflow inlet slot, and has a respective downstream surface at a point where said sampled airflow exits said sampled airflow inlet slot; wherein each of said sides has a smoothly varying convex profile that extends at least most of a distance between said respective upstream and downstream surfaces of each of said sides; wherein a pressure drop is produced when said sampled airflow flows through said sampled airflow inlet slot and is divided by said secondary airflow inlet slot into said left primary airflow, said right primary airflow, and said secondary airflow; and wherein said pressure drop is minimized by said smoothly varying convex profiles of said sides as compared to if said sides did not have said smoothly varying convex profiles.

7. The concentrator of claim 6, wherein said air processor further comprises a pair of rods; wherein each said rod has an at least generally semicircular cross sectional configuration, and wherein each said rod comprises a respective one of said sides of said sampled airflow inlet slot.

8. The concentrator of claim 1, wherein said air processor further comprises at least one blade and a hollow outer hub having an outer hub central cavity; wherein said blade comprises said sampled airflow inlet slot and said secondary airflow inlet slot; wherein said sampled airflow inlet slot of said blade is located in said outer hub; wherein said left and right primary airflows flow into said outer hub central cavity; wherein said air processor further comprises a pair of end plates; wherein one of said end plates comprises a primary airflow outlet that is in fluid communication with said outer hub central cavity; and wherein at least part of said left and right primary airflows flow out of said outer hub central cavity through said primary airflow outlet.

9. The concentrator of claim 8, wherein said air processor further comprises an inner hub having an inner hub central cavity; wherein one of said end plates comprises an end plate secondary airflow outlet that is in fluid communication with said inner hub central cavity; wherein said blade extends between said inner and outer hubs; wherein said blade comprises a blade secondary airflow outlet port; wherein said secondary airflow flows from said blade secondary airflow outlet port into said inner hub central cavity; and wherein said secondary airflow flows out of said inner hub central cavity through said end plate secondary airflow outlet.

10. The concentrator of claim 9, wherein said air processor further comprises a fan that is operable to apply a respective negative air pressure to said primary airflows and to said secondary airflow; wherein said negative air pressure of said primary airflows is greater than said negative air pressure of said secondary airflow, to provide a negative pressure difference between said primary airflows and said secondary airflow; wherein said air processor further comprises a filter assembly: wherein said filter assembly comprises a filter; wherein said filter assembly is operable to use said negative pressure difference to urge said secondary airflow to flow out of said end plate secondary airflow outlet and through said filter; and wherein said filter is operable to remove at least some of said particles containing target material from said secondary airflow that flows out of said end plate secondary airflow outlet.

11. The concentrator of claim 10, wherein said end plate secondary airflow outlet is in fluid communication with said outer hub central cavity; and wherein said filter assembly further comprises a filter adapter that is operable to provide said fluid communication between said end plate secondary airflow outlet and said outer hub central cavity.

12. The concentrator of claim 8, wherein said concentrator further comprises a fan that is operable to urge said primary airflows to flow out of said outer hub central cavity through said primary airflow outlet.

13. The concentrator of claim 12, wherein said concentrator further comprises a fan plenum for said fan; wherein said fan plenum has a central longitudinal axis; wherein said fan is operable to urge said primary airflows to flow out of said concentrator as a jet of air that flows at least generally parallel to said axis; wherein said concentrator has a circular sensing radius; wherein said jet of air produces an induced draft effect around said concentrator; and wherein said induced draft effect increases said circular sensing radius to a size that is greater than would be the case if said concentrator did not produce said induced draft effect.

14. The concentrator of claim 1, wherein said air processor further comprises a central longitudinal axis; a hollow outer hub; and at least two blades; wherein each said blade comprises a respective said sampled airflow inlet slot and a respective said secondary airflow inlet slot; wherein said sampled airflow inlet slot of each said blade is located in said outer hub; and wherein said at least two blades are radially arranged about said axis.

15. The concentrator of claim 14, wherein said outer hub has an outer surface; wherein said concentrator further comprises a hollow shroud that is operable to provide an air chamber around at least a portion of said outer surface of said outer hub; wherein said air chamber is in fluid communication with said sampled airflow inlet slot of each said blade; and wherein said shroud comprises a shroud inlet that is operable to receive said sampled airflow.

16. The concentrator of claim 15, wherein said shroud comprises an at least generally cylindrical shroud outer wall; and wherein said shroud inlet is located in said shroud outer wall.

17. The concentrator of claim 15, wherein said shroud comprises a shroud end surface; and wherein said shroud inlet is located in said shroud end surface.

18. The concentrator of claim 8, wherein said air processor further comprises an inner hub and a fan; wherein said inner hub has an inner hub central cavity; wherein said blade extends between said inner and outer hubs; wherein said blade comprises a blade secondary airflow outlet port; wherein said secondary airflow flows from said blade secondary airflow outlet port into said inner hub central cavity;

wherein said fan is operable to apply a respective negative air pressure to said primary airflows and to said secondary airflow; wherein said respective negative air pressures of said primary airflows are greater than said respective negative air pressure of said secondary airflow, to provide a negative pressure difference between said primary airflows and said secondary airflow; wherein said air processor further comprises a filter assembly; wherein said filter assembly comprises a filter; wherein said filter assembly is operable to use said negative pressure difference to urge said secondary airflow to flow out of said inner hub central cavity and through said filter; and wherein said filter is operable to remove at least some of said particles containing target material from said secondary airflow that flows out of said inner hub central cavity.

19. The concentrator of claim 6, wherein said air processor further comprises a sampled airflow inlet pocket comprising concave left and right sampled airflow inlet lobes through which at least part of said sampled airflow flows before entering said sampled airflow inlet slot; and wherein each of said sampled airflow inlet lobes has a curved profile and is operable to impart a rotary motion to a respective part of said sampled airflow.

20. The concentrator of claim 6, wherein said left and right primary airflows have a combined flow rate; wherein said secondary air flow has a flow rate; and wherein said flow rate of said secondary air flow is less than about 1% of said combined flow rate of said primary airflows.

21. A concentrator, wherein said concentrator comprises an air processor that comprises:

a sampled airflow inlet slot that is operable to receive a sampled airflow that contains particles containing target material; and a secondary airflow inlet slot that is located downstream from said sampled airflow inlet slot;

wherein said sampled airflow inlet slot is operable to use centrifugal force to concentrate at least some of said particles containing target material into a central portion of said sampled airflow as said sampled airflow flows through said sampled airflow inlet slot;

wherein said sampled airflow inlet slot is operable to produce a non-collimated sampled airflow as said sampled airflow flows through said sampled airflow inlet slot;

wherein said sampled airflow inlet slot and said secondary airflow inlet slot share a common plane of symmetry;

wherein said secondary airflow inlet slot is operable to divide a secondary airflow from at least a part of said central portion of said sampled airflow that is received by said secondary airflow inlet slot from said sampled airflow inlet slot, is operable to divide a left primary airflow from at least a part of a left portion of said sampled airflow that is received by said secondary airflow inlet slot from said sampled airflow inlet slot, and is operable to divide a right primary airflow from at least a part of a right portion of said sampled airflow that is received by said secondary airflow inlet slot from said sampled airflow inlet slot;

wherein said secondary airflow flows through said secondary airflow inlet slot;

wherein said sampled airflow inlet slot has a pair of sides; wherein each of said sides has a respective upstream surface at a point where said sampled airflow enters said sampled airflow inlet slot, and has a respective downstream surface at a point where said sampled airflow exits said sampled airflow inlet slot; wherein each of said sides has a smoothly varying convex profile that extends at least most of a distance between its-said respective upstream and downstream surfaces of each of said sides; wherein a pressure drop is produced when said sampled airflow flows through said sampled airflow inlet slot and is divided by said secondary airflow inlet slot into said left primary airflow, said right primary airflow, and said secondary airflow; wherein said pressure drop is minimized by said smoothly varying convex profiles of said sides as compared to if said sides did not have said smoothly varying convex profiles;

wherein said air processor further comprises a central longitudinal axis and at least two blades; wherein each said blade comprises a respective said sampled airflow inlet slot; a respective said secondary airflow inlet slot, and a respective blade secondary airflow outlet port; wherein a respective said secondary airflow exits from each said blade secondary airflow outlet port; wherein said blades are radially arranged about said axis; and wherein said respective said secondary airflows flow radially inwardly toward each other and toward said axis.

22. A concentrator, wherein said concentrator comprises an air processor that comprises:

a sampled airflow inlet slot that is operable to receive a sampled airflow that contains particles containing target material; and a secondary airflow inlet slot that is located downstream from said sampled airflow inlet slot;

wherein said sampled airflow inlet slot is operable to use centrifugal force to concentrate at least some of said particles containing target material into a central portion of said sampled airflow as said sampled airflow flows through said sampled airflow inlet slot;

wherein said sampled airflow inlet slot is operable to produce a non-collimated sampled airflow as said sampled airflow flows through said sampled airflow inlet slot;

wherein said sampled airflow inlet slot and said secondary airflow inlet slot share a common plane of symmetry;

wherein said secondary airflow inlet slot is operable to divide a secondary airflow from at least a part of said central portion of said sampled airflow that is received by said secondary airflow inlet slot from said sampled airflow inlet slot, is operable to divide a left primary airflow from at least a part of a left portion of said sampled airflow that is received by said secondary airflow inlet slot from said sampled airflow inlet slot, and is operable to divide a right primary airflow from at least a part of a right portion of said sampled airflow that is received by said secondary airflow inlet slot from said sampled airflow inlet slot;

wherein said secondary airflow flows through said secondary airflow inlet slot;

wherein said sampled airflow inlet slot has a pair of sides; wherein each of said sides has a respective upstream surface at a point where said sampled airflow enters said sampled airflow inlet slot, and has a respective downstream surface at a point where said sampled airflow exits said sampled airflow inlet slot; wherein each of said sides has a smoothly varying convex profile that extends at least most of a distance between its-said respective upstream and downstream surfaces of each of said sides; wherein a pressure drop is produced when said sampled airflow flows through said sampled airflow inlet slot and is divided by said secondary airflow inlet slot into said left primary airflow, said right primary airflow, and said secondary airflow; wherein said pressure drop is minimized by said smoothly varying convex profiles of said sides as compared to if said sides did not have said smoothly varying convex profiles;

wherein said air processor further comprises at least one blade and a hollow outer hub having an outer hub central cavity; wherein said blade comprises said sampled airflow inlet slot and said secondary airflow inlet slot; wherein said sampled airflow inlet slot of said blade is located in said outer hub; wherein said left and right primary airflows flow into said outer hub central cavity; wherein said air processor further comprises a pair of end plates; wherein one of said end plates comprises a primary airflow outlet that is in fluid communication with said outer hub central cavity; and wherein at least part of said left and right primary airflows flow out of said outer hub central cavity through said primary airflow outlet.

23. The concentrator of claim 22, wherein said air processor further comprises an inner hub having an inner hub central cavity; wherein one of said end plates comprises an end plate secondary airflow outlet that is in fluid communication with said inner hub central cavity; wherein said blade extends between said inner and outer hubs; wherein said blade comprises a blade secondary airflow outlet port; wherein said secondary airflow flows from said blade secondary airflow outlet port into said inner hub central cavity; and wherein said secondary airflow flows out of said inner hub central cavity through said end plate secondary airflow outlet.

24. The concentrator of claim 23, wherein said air processor further comprises a fan that is operable to apply a respective negative air pressure to said primary airflows and to said secondary airflow; wherein said negative air pressure of said primary airflows is greater than said negative air pressure of said secondary airflow, to provide a negative pressure difference between said primary airflows and said secondary airflow; wherein said air processor further comprises a filter assembly; wherein said filter assembly comprises a filter; wherein said filter assembly is operable to use said negative pressure difference to urge said secondary airflow to flow out of said end plate secondary airflow outlet and through said filter; and wherein said filter is operable to remove at least some of said particles containing target material from said secondary airflow that flows out of said end plate secondary airflow outlet.

25. The concentrator of claim 24, wherein said end plate secondary airflow outlet is in fluid communication with said outer hub central cavity; and wherein said filter assembly further comprises a filter adapter that is operable to provide said fluid communication between said end plate secondary airflow outlet and said outer hub central cavity.

26. The concentrator of claim 22, wherein said concentrator further comprises a fan that is operable to urge said primary airflows to flow out of said outer hub central cavity through said primary airflow outlet.

27. The concentrator of claim 26, wherein said concentrator further comprises a fan plenum for said fan; wherein said fan plenum has a central longitudinal axis; wherein said fan is operable to urge said primary airflows to flow out of said concentrator as a jet of air that flows at least generally parallel to said axis; wherein said concentrator has a circular sensing radius; wherein said jet of air produces an induced draft effect around said concentrator; and wherein said induced draft effect increases said circular sensing radius to a size that is greater than would be the case if said concentrator did not produce said induced draft effect.

28. A concentrator, wherein said concentrator comprises an air processor that comprises:

a sampled airflow inlet slot that is operable to receive a sampled airflow that contains particles containing target material; and a secondary airflow inlet slot that is located downstream from said sampled airflow inlet slot;

wherein said sampled airflow inlet slot is operable to use centrifugal force to concentrate at least some of said particles containing target material into a central portion of said sampled airflow as said sampled airflow flows through said sampled airflow inlet slot;

wherein said sampled airflow inlet slot is operable to produce a non-collimated sampled airflow as said sampled airflow flows through said sampled airflow inlet slot;

wherein said sampled airflow inlet slot and said secondary airflow inlet slot share a common plane of symmetry;

wherein said secondary airflow inlet slot is operable to divide a secondary airflow from at least a part of said central portion of said sampled airflow that is received by said secondary airflow inlet slot from said sampled airflow inlet slot, is operable to divide a left primary airflow from at least a part of a left portion of said sampled airflow that is received by said secondary airflow inlet slot from said sampled airflow inlet slot, and is operable to divide a right primary airflow from at least a part of a right portion of said sampled airflow that is received by said secondary airflow inlet slot from said sampled airflow inlet slot;

wherein said secondary airflow flows through said secondary airflow inlet slot;

wherein said sampled airflow inlet slot has a pair of sides; wherein each of said sides has a respective upstream surface at a point where said sampled airflow enters said sampled airflow inlet slot, and has a respective downstream surface at a point where said sampled airflow exits said sampled airflow inlet slot; wherein each of said sides has a smoothly varying convex profile that extends at least most of a distance between said respective upstream and downstream surfaces of each of said sides; wherein a pressure drop is produced when said sampled airflow flows through said sampled airflow inlet slot and is divided by said secondary airflow inlet slot into said left primary airflow, said right primary airflow, and said secondary airflow; wherein said pressure drop is minimized by said smoothly varying convex profiles of said sides as compared to if said sides did not have said smoothly varying convex profiles;

wherein said air processor further comprises a central longitudinal axis; a hollow outer hub; and at least two blades; wherein each said blade comprises a respective said sampled airflow inlet slot and a respective said secondary airflow inlet slot; wherein said sampled airflow inlet slot of each said blade is located in said outer hub; and wherein said at least two blades are radially arranged about said axis.

29. The concentrator of claim 28, wherein said outer hub has an outer surface; wherein said concentrator further comprises a hollow shroud that is operable to provide an air chamber around at least a portion of said outer surface of said outer hub; wherein said air chamber is in fluid communication with said sampled airflow inlet slot of each said blade; and wherein said shroud comprises a shroud inlet that is operable to receive said sampled airflow.

30. The concentrator of claim 29, wherein said shroud comprises an at least generally cylindrical shroud outer wall; and wherein said shroud inlet is located in said shroud outer wall.

31. The concentrator of claim 29, wherein said shroud comprises a shroud end surface; and wherein said shroud inlet is located in said shroud end surface.

32. The concentrator of claim 22, wherein said air processor further comprises and inner hub and a fan; wherein said inner hub has an inner hub central cavity; wherein said blade extends between said inner and outer hubs; wherein said blade comprises a blade secondary airflow outlet port; wherein said secondary airflow flows from said blade secondary airflow outlet port into said inner hub central cavity; wherein said fan is operable to apply a respective negative air pressure to said primary airflows and to said secondary airflow; wherein said respective negative air pressures of said primary airflows are greater than said respective negative air pressure of said secondary airflow, to provide a negative pressure difference between said primary airflows and said secondary airflow; wherein said air processor further comprises a filter assembly; wherein said filter assembly comprises a filter; wherein said filter assembly is operable to use said negative pressure difference to urge said secondary airflow to flow out of said inner hub central cavity and through said filter; and wherein said filter is operable to remove at least some of said particles containing target material from said secondary airflow that flows out of said inner hub central cavity.

33. The concentrator of claim 1, wherein said left and right primary airflows have a combined flow rate; wherein said secondary air flow has a flow rate; and wherein said flow rate of said secondary air flow is less than about 10% of said combined flow rate of said primary airflows.

34. The concentrator of claim 6, wherein said left and right primary airflows have a combined flow rate; wherein said secondary air flow has a flow rate; and wherein said flow rate of said secondary air flow is less than about 10% of said combined flow rate of said primary airflows.

35. The concentrator of claim 1, wherein said air processor further comprises at least one blade;

wherein said blade comprises said sampled airflow inlet slot; said secondary airflow inlet slot, and a respective blade secondary airflow outlet port;

wherein said blade further comprises a secondary airflow channel that is located downstream from said secondary airflow inlet slot; wherein said secondary airflow channel has a width; and wherein said width gradually increases from said secondary airflow inlet slot to a point in said secondary airflow channel that is located substantially downstream from said secondary airflow inlet slot.

36. The concentrator of claim 6, wherein said smoothly varying convex profile has an angular extent; and wherein said angular extent is at least about 180 degrees.

37. The concentrator of claim 1, wherein said sampled airflow inlet slot has an upstream end and a downstream end, and comprises a pair of opposing sides; wherein there is a distance between corresponding opposing parts of said opposing sides; and wherein said distance first gets gradually smaller in size and then gets gradually larger in size from said upstream end to said downstream end of said sampled airflow inlet slot.

* * * * *